US008378071B2

(12) United States Patent
Khleif et al.

(10) Patent No.: US 8,378,071 B2
(45) Date of Patent: Feb. 19, 2013

(54) PEPTIDE EPITOPES OF VEGFR-2/KDR THAT INHIBIT ANGIOGENESIS

(75) Inventors: Samir N. Khleif, Silverspring, MD (US); Yujun Dong, Washington, DC (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 806 days.

(21) Appl. No.: 12/402,401

(22) Filed: Mar. 11, 2009

(65) Prior Publication Data

US 2009/0247467 A1    Oct. 1, 2009

Related U.S. Application Data

(63) Continuation of application No. 11/404,555, filed on Apr. 14, 2006, now abandoned.

(60) Provisional application No. 60/671,867, filed on Apr. 15, 2005.

(51) Int. Cl.
| A61K 38/00 | (2006.01) |
| A61K 38/04 | (2006.01) |
| A61K 47/00 | (2006.01) |
| A61K 51/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |

(52) U.S. Cl. ........ 530/328; 530/327; 530/326; 530/325; 530/324; 530/333; 514/1.1; 514/1.2; 424/1.69

(58) Field of Classification Search .................. None
See application file for complete search history.

(56) References Cited

U.S. PATENT DOCUMENTS

| 5,837,231 A | 11/1998 | Low et al. |
| 5,955,311 A | 9/1999 | Rockwell et al. |
| 6,080,728 A | 6/2000 | Mixson |
| 6,251,603 B1 | 6/2001 | Jager et al. |
| 6,559,126 B2 | 5/2003 | Tournaire et al. |
| 6,777,534 B1 | 8/2004 | Klagsbrun et al. |
| 6,833,349 B2 | 12/2004 | Xia et al. |
| 2004/0266688 A1* | 12/2004 | Nayak .............................. 514/12 |
| 2006/0216301 A1 | 9/2006 | Tahara et al. |
| 2009/0075304 A1* | 3/2009 | Weidanz et al. ............. 435/7.24 |
| 2009/0233318 A1* | 9/2009 | Weidanz ....................... 435/7.24 |
| 2009/0304679 A1* | 12/2009 | Weidanz .................... 424/130.1 |

FOREIGN PATENT DOCUMENTS
| WO | WO 03/075840 A2 | 9/2003 |
| WO | WO 2004/024766 A1 | 3/2004 |

OTHER PUBLICATIONS

Binétruy-Tournaire et al., "Identification of a peptide blocking vascular endothelial growth factor (VEGF)-mediated angiogenesis," The EMBO Journal, 19(7):1525-1533 (2000).
Bradney et al., "Cytokines as Adjuvants for the Induction of Anti-Human Immunodeficiency Virus Peptide Immunoglobulin G (IgG) and IgA Antibodies in Serum and Mucosal Secretions after Nasal Immunization," Journal of Virology, 76(2):517-524, (Jan. 2002).
Brander and Walker, "The HLA Class I Restricted CTL Response in HIV-1 Infection: Systematic Identification of Optimal Eptiopes," AIDS Res. Center and Harvard Medical School, 1996.
Dong et al., "Identification of H-2Db-Specific CD8+ T-cell epiotopes from mouse VEGFR2 that can inhibit angiogenesis and tumor growth," J Immunother, 29(1):32-40, (2006).
Dvorak et al., "Vascular permeability factor/vascular endothelial growth factor: an important mediator of angiogenesis in malignancy and inflammation," Int. Arch. Allergy Immunol., 107(1-3):233-5, (1995). (Abstract only).
Ferrara et al., "The biology of VEGF and its receptors," Nature Med., 9(6):669-676, 2003.
Ikeda et al., "Expression of vascular endothelial growth factor isoforms and their receptors Flt-1, KDR, and neuropilin-1 in synovial tissues of rheumatoid arthritis," J. Pathol., 191(4):426-33, (Aug. 2000). (Abstract only).
Ishizaki et al., "Inhibition of Tumor Growth with Antiangiogenic Cancer Vaccine Using Epitope Peptides Derived from Human Vascular Endothelial Growth Factor Receptor 1," Clinical Cancer Research, 12(19):5841-5849, (Oct. 1, 2006).
Kono et al., "Dendritic Cells Pulsed with HER-2/neu-derived Peptides Can Induce Specific T-Cell Responses in Patients with Gastric Cancer1," Clinical Cancer Research; vol. 8, pp. 3394-3400 (Nov. 2002).
Kou et al., "In vivo inhibition of tumor angiogenesis by a soluble VEGFR-2 fragment," Exp Mol Pathology, 76(2):129-37, (Apr. 2004). (Abstract only).
Li et al., "Active Immunization Against the Vascular Endothelial Growth Factor Receptor flk 1 Inhibits Tumor Angiogenesis and Metastasis," J. Exp. Med., 195(12):1575-1584, (Jun. 17, 2002).
Li et al., "Production of neutralizing monoclonal antibody against human vascular endothelial growth factor receptor II," Acta Pharmacol Sin, 25(10):1292-1298, (Oct. 2004).
Lu et al., "Complete inhibition of vascular endothelial growth factor (VEGF) activities with a bifunctional diabody directed against both VEGF kinase receptors, fms-like tyrosine kinase receptor and kinase insert domain-containing receptor," Cancer Research, 61(19):7002-8, (Oct. 1, 2001). (Abstract only).
Lu et al., "Selection of high affinity human neutralizing antibodies to VEGFR2 from a large antibody phage display library for antiangiogenesis therapy," Int J. Cancer, 97(3):393-9, (Jan. 20, 2002). (Abstract only).

(Continued)

Primary Examiner — Maury Audet
(74) Attorney, Agent, or Firm — Klarquist Sparkman, LLP

(57) ABSTRACT

The disclosure provides antigenic peptides of Vascular Endothelial Growth Factor Receptor 2(VEGFR-2)/KDR. Pharmaceutical compositions including the peptides and/or antigen presenting cells that exhibit the VEGFR-2/KDR peptides on their cell surface are also provided. Methods for eliciting an immune response and for inhibiting angiogenesis by administering such pharmaceutical compositions are provided.

10 Claims, 8 Drawing Sheets

OTHER PUBLICATIONS

Lu et al., "Tailoring in vitro selection for a picomolar affinity human antibody directed against vascular endothelial growth factor receptor 2 for enhanced neutralizing activity," J. Biology Chem, 278(44):43496-507, (Oct. 31, 2003). (Abstract only).

McMahon, "VEGF Receptor Signaling in Tumor Angiogenesis," The Oncologist, 5(suppl 1):3-10 (2005).

Nair et al., "Synergy between tumor immunotherapy and antiangiogenic therapy," Immunobiology, 102(3):964-971, (Aug. 1, 2003).

NCBI Accession No. P35918 "Vascular endothelial growth factor receptor 2 precursor (VEGFR-2) (Protein-tyrosine kinase receptor Flk-1) (Fetal liver kinase 1)," (May 1, 2000).

NCBI Accession No. P35968 "Vascular endothelial growth factor receptor 2 precursor (VEGFR-2) (Kinase insert domain receptor) (Protein-tyrosine kinase receptor Flk-1)," (May 1, 2000).

Neufeld et al., "Vascular endothelial growth factor (VEGF) and its receptors," The FASEB Journal, 13:9-22, (Jan. 1999).

Niethammer et al., "A DNA vaccine against VEGF receptor 2 prevents effective angiogenesis and inhibits tumor growth," Nature Med., 8(12):1369-1375, 2002.

O'Neill et al., "Generation of autologous peptide- and protein-pulsed dendritic cells for patient-specific immunotherapy," Methods Mol Med., 109:97-112, (2005). (Abstract only).

Online Medical Directory; http://cancerweb.ncl.ac.uk/cgi-bin/omd?query=adjuvant; (Nov. 18, 1997).

Pan et al., "Enhanced antimetastatic effect of fetal liver kinase 1 extracellular domain and interferon-gamma fusion gene-modified dendritic cell vaccination," Gene Therapy, pp. 1-9, (2005).

Parker et al., "Scheme for ranking potential HLA-A2 binding peptides based on independent binding of individual peptide sidechains," 152(1):163-175, 1994.

Paz and Zhu, "Development of Angiogenesis Inhibitors to Vascular Endothelial Growth Factor Receptor 2, Current Status and Future Perspective," Frontiers in Bioscience, 10:1415-1439, (May 1, 2005).

Prewett et al., "Antivascular endothelial growth factor receptor (fetal liver kinase 1) monoclonal antibody inhibits tumor angiogenesis and growth of several mouse and human tumors," Cancer Res., 59(20):5209-5218, 1999.

Rammensee et al., "MHC ligands and peptide motifs: first listing," Immunogenetics, 41(4):178-228, 1995.

Rammensee et al., "SYFPEITHI: database for MHC ligands and peptide motifs," Immunogenetics, 50(3-4):213-219, 1999.

Schlaeppi et al., "Characterization of a new product, in vivo neutralizing monoclonal antibody to human vascular endothelial growth factor," J. Cancer Research Clinic Oncology, 125(6):336-42, (1999). (Abstract only).

Shibuya, "VEGF-receptor inhibitors for anti-angiogenesis," Nippon Yakurigaku Zasshi, 122(6):498-503. (Dec. 2003). (Abstract only).

Strawn et al., "Flk-1 as a target for tumor growth inhibition," Cancer Research, 56(15):3540-5, (Aug. 1, 1996). (Abstract only).

Wada et al., "Mechanism for cancer immunotherapy targeting tumor-angiogensis," Abstract Only, Apr. 17, 2005.

Wada et al., "Rationale for antiangiogenic cancer therapy with vaccination using epitope peptides derived from human vascular endothelial growth factor receptor 2," Cancer Res., 65(11):4939-4946, 2005.

Wei et al., "Immunotherapy of tumors with xenogeneic endothelial cells as a vaccine," Nature Med., 6(10):1160-1166, 2000.

Yoshiji et al., "Halting the interaction between vascular endothelial growth factor and its receptors attenuates liver carcinogenesis in mice," Hepatology, 39(6):1517-24, (Jun. 2004). (Abstract only).

Zhang et al., "A monoclonal antibody that blocks VEGF binding to VEGFR2 (KDR/Flk-1) inhibits vascular expression of Flk-1 and tumor growth in an orthotopic human breast cancer model," Angiogenesis, 5(1-2):35-44, (2002). (Abstract only).

Zhu and Witte, "Inhibition of tumor growth and metastasis by targeting tumor-associated angiogenesis with antagonists to the receptors of vascular endothelial growth factor," Invest New Drugs, 17(3):195-212, (1999). (Abstract only).

Zhu et al., "Clinical Development of Angiogenesis Inhibitors to Vascular Endothelial Growth Factor and Its Receptors as Cancer Therapeutics," Current Cancer Drug Targets, 2:135-156, (2002).

Zhu et al., "Inhibition of vascular endothelial growth factor-induced receptor activation with anti-kinase insert domain-containing receptor single-chain antibodies from a phage display library," Cancer Res., 58(15):3209-3214, 1998.

* cited by examiner

US 8,378,071 B2

SEQUENCE LISTING

```
<160> NUMBER OF SEQ ID NOS: 13

<210> SEQ ID NO 1
<211> LENGTH: 1367
<212> TYPE: PRT
<213> ORGANISM: Mus musculus

<400> SEQUENCE: 1

Met Glu Ser Lys Ala Leu Leu Ala Val Ala Leu Trp Phe Cys Val Glu
1               5                   10                  15

Thr Arg Ala Ala Ser Val Gly Leu Pro Gly Asp Phe Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
    50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
            100                 105                 110

Ala Ser Thr Val Tyr Val Tyr Val Arg Asp Tyr Arg Ser Pro Phe Ile
        115                 120                 125

Ala Ser Val Ser Asp Gln His Gly Ile Val Tyr Ile Thr Glu Asn Lys
    130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                165                 170                 175

Asn Arg Ile Ser Trp Asp Ser Glu Ile Gly Phe Thr Leu Pro Ser Tyr
            180                 185                 190

Met Ile Ser Tyr Ala Gly Met Val Phe Cys Glu Ala Lys Ile Asn Asp
        195                 200                 205

Glu Thr Tyr Gln Ser Ile Met Tyr Ile Val Val Val Gly Tyr Arg
    210                 215                 220

Ile Tyr Asp Val Ile Leu Ser Pro Pro His Glu Ile Glu Leu Ser Ala
```

```
                225                 230                 235                 240
Gly Glu Lys Leu Val Leu Asn Cys Thr Ala Arg Thr Glu Leu Asn Val
                245                 250                 255

Gly Leu Asp Phe Thr Trp His Ser Pro Pro Ser Lys Ser His His Lys
            260                 265                 270

Lys Ile Val Asn Arg Asp Val Lys Pro Phe Pro Gly Thr Val Ala Lys
        275                 280                 285

Met Phe Leu Ser Thr Leu Thr Ile Glu Ser Val Thr Lys Ser Asp Gln
    290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
                325                 330                 335

Gly Met Lys Ser Leu Val Glu Ala Thr Val Gly Ser Gln Val Arg Ile
            340                 345                 350

Pro Val Lys Tyr Leu Ser Tyr Pro Ala Pro Asp Ile Lys Trp Tyr Arg
        355                 360                 365

Asn Gly Arg Pro Ile Glu Ser Asn Tyr Thr Met Ile Val Gly Asp Glu
    370                 375                 380

Leu Thr Ile Met Glu Val Thr Glu Arg Asp Ala Gly Asn Tyr Thr Val
385                 390                 395                 400

Ile Leu Thr Asn Pro Ile Ser Met Glu Lys Gln Ser His Met Val Ser
                405                 410                 415

Leu Val Val Asn Val Pro Pro Gln Ile Gly Glu Lys Ala Leu Ile Ser
            420                 425                 430

Pro Met Asp Ser Tyr Gln Tyr Gly Thr Met Gln Thr Leu Thr Cys Thr
        435                 440                 445

Val Tyr Ala Asn Pro Pro Leu His His Ile Gln Trp Tyr Trp Gln Leu
    450                 455                 460

Glu Glu Ala Cys Ser Tyr Arg Pro Gly Gln Thr Ser Pro Tyr Ala Cys
465                 470                 475                 480

Lys Glu Trp Arg His Val Glu Asp Phe Gln Gly Gly Asn Lys Ile Glu
                485                 490                 495

Val Thr Lys Asn Gln Tyr Ala Leu Ile Glu Gly Lys Asn Lys Thr Val
            500                 505                 510

Ser Thr Leu Val Ile Gln Ala Ala Asn Val Ser Ala Leu Tyr Lys Cys
        515                 520                 525

Glu Ala Ile Asn Lys Ala Gly Arg Gly Glu Arg Val Ile Ser Phe His
    530                 535                 540

Val Ile Arg Gly Pro Glu Ile Thr Val Gln Pro Ala Ala Gln Pro Thr
545                 550                 555                 560

Glu Gln Glu Ser Val Ser Leu Leu Cys Thr Ala Asp Arg Asn Thr Phe
                565                 570                 575

Glu Asn Leu Thr Trp Tyr Lys Leu Gly Ser Gln Ala Thr Ser Val His
            580                 585                 590

Met Gly Glu Ser Leu Thr Pro Val Cys Lys Asn Leu Asp Ala Leu Trp
        595                 600                 605

Lys Leu Asn Gly Thr Met Phe Ser Asn Ser Thr Asn Asp Ile Leu Ile
    610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
                645                 650                 655
```

```
Leu Ile Ile Leu Glu Arg Met Ala Pro Met Ile Thr Gly Asn Leu Glu
            660                 665                 670

Asn Gln Thr Thr Thr Ile Gly Glu Thr Ile Glu Val Thr Cys Pro Ala
        675                 680                 685

Ser Gly Asn Pro Thr Pro His Ile Thr Trp Phe Lys Asp Asn Glu Thr
690                 695                 700

Leu Val Glu Asp Ser Gly Ile Val Leu Arg Asp Gly Asn Arg Asn Leu
705                 710                 715                 720

Thr Ile Arg Arg Val Arg Lys Glu Asp Gly Gly Leu Tyr Thr Cys Gln
                725                 730                 735

Ala Cys Asn Val Leu Gly Cys Ala Arg Ala Glu Thr Leu Phe Ile Ile
            740                 745                 750

Glu Gly Ala Gln Glu Lys Thr Asn Leu Glu Val Ile Ile Leu Val Gly
        755                 760                 765

Thr Ala Val Ile Ala Met Phe Phe Trp Leu Leu Leu Val Ile Leu Val
770                 775                 780

Arg Thr Val Lys Arg Ala Asn Glu Gly Glu Leu Lys Thr Gly Tyr Leu
785                 790                 795                 800

Ser Ile Val Met Asp Pro Asp Glu Leu Pro Leu Asp Glu Arg Cys Glu
                805                 810                 815

Arg Leu Pro Tyr Asp Ala Ser Lys Trp Glu Phe Pro Arg Asp Arg Leu
            820                 825                 830

Lys Leu Gly Lys Pro Leu Gly Arg Gly Ala Phe Gly Gln Val Ile Glu
        835                 840                 845

Ala Asp Ala Phe Gly Ile Asp Lys Thr Ala Thr Cys Lys Thr Val Ala
850                 855                 860

Val Lys Met Leu Lys Glu Gly Ala Thr His Ser Glu His Arg Ala Leu
865                 870                 875                 880

Met Ser Glu Leu Lys Ile Leu Ile His Ile Gly His His Leu Asn Val
                885                 890                 895

Val Asn Leu Leu Gly Ala Cys Thr Lys Pro Gly Gly Pro Leu Met Val
            900                 905                 910

Ile Val Glu Phe Ser Lys Phe Gly Asn Leu Ser Thr Tyr Leu Arg Gly
        915                 920                 925

Lys Arg Asn Glu Phe Val Pro Tyr Lys Ser Lys Gly Ala Arg Phe Arg
930                 935                 940

Gln Gly Lys Asp Tyr Val Gly Glu Leu Ser Val Asp Leu Lys Arg Arg
945                 950                 955                 960

Leu Asp Ser Ile Thr Ser Ser Gln Ser Ser Ala Ser Ser Gly Phe Val
                965                 970                 975

Glu Glu Lys Ser Leu Ser Asp Val Glu Glu Glu Glu Ala Ser Glu Glu
            980                 985                 990

Leu Tyr Lys Asp Phe Leu Thr Leu Glu His Leu Ile Cys Tyr Ser Phe
        995                 1000                1005

Gln Val Ala Lys Gly Met Glu Phe Leu Ala Ser Arg Lys Cys Ile
        1010                1015                1020

His Arg Asp Leu Ala Ala Arg Asn Ile Leu Leu Ser Glu Lys Asn
        1025                1030                1035

Val Val Lys Ile Cys Asp Phe Gly Leu Ala Arg Asp Ile Tyr Lys
        1040                1045                1050

Asp Pro Asp Tyr Val Arg Lys Gly Asp Ala Arg Leu Pro Leu Lys
        1055                1060                1065

Trp Met Ala Pro Glu Thr Ile Phe Asp Arg Val Tyr Thr Ile Gln
        1070                1075                1080
```

-continued

```
Ser Asp Val Trp Ser Phe Gly Val Leu Leu Trp Glu Ile Phe Ser
    1085                1090                1095

Leu Gly Ala Ser Pro Tyr Pro Gly Val Lys Ile Asp Glu Glu Phe
    1100                1105                1110

Cys Arg Arg Leu Lys Glu Gly Thr Arg Met Arg Ala Pro Asp Tyr
    1115                1120                1125

Thr Thr Pro Glu Met Tyr Gln Thr Met Leu Asp Cys Trp His Glu
    1130                1135                1140

Asp Pro Asn Gln Arg Pro Ser Phe Ser Glu Leu Val Glu His Leu
    1145                1150                1155

Gly Asn Leu Leu Gln Ala Asn Ala Gln Gln Asp Gly Lys Asp Tyr
    1160                1165                1170

Ile Val Leu Pro Met Ser Glu Thr Leu Ser Met Glu Glu Asp Ser
    1175                1180                1185

Gly Leu Ser Leu Pro Thr Ser Pro Val Ser Cys Met Glu Glu Glu
    1190                1195                1200

Glu Val Cys Asp Pro Lys Phe His Tyr Asp Asn Thr Ala Gly Ile
    1205                1210                1215

Ser His Tyr Leu Gln Asn Ser Lys Arg Lys Ser Arg Pro Val Ser
    1220                1225                1230

Val Lys Thr Phe Glu Asp Ile Pro Leu Glu Glu Pro Glu Val Lys
    1235                1240                1245

Val Ile Pro Asp Asp Ser Gln Thr Asp Ser Gly Met Val Leu Ala
    1250                1255                1260

Ser Glu Glu Leu Lys Thr Leu Glu Asp Arg Asn Lys Leu Ser Pro
    1265                1270                1275

Ser Phe Gly Gly Met Met Pro Ser Lys Ser Arg Glu Ser Val Ala
    1280                1285                1290

Ser Glu Gly Ser Asn Gln Thr Ser Gly Tyr Gln Ser Gly Tyr His
    1295                1300                1305

Ser Asp Asp Thr Asp Thr Thr Val Tyr Ser Ser Asp Glu Ala Gly
    1310                1315                1320

Leu Leu Lys Met Val Asp Ala Ala Val His Ala Asp Ser Gly Thr
    1325                1330                1335

Thr Leu Gln Leu Thr Ser Cys Leu Asn Gly Ser Gly Pro Val Pro
    1340                1345                1350

Ala Pro Pro Pro Thr Pro Gly Asn His Glu Arg Gly Ala Ala
    1355                1360                1365

<210> SEQ ID NO 2
<211> LENGTH: 1356
<212> TYPE: PRT
<213> ORGANISM: Homo sapiens

<400> SEQUENCE: 2

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80
```

```
Asp Gly Leu Phe Cys Lys Thr Leu Thr Ile Pro Lys Val Ile Gly Asn
                85                  90                  95
Asp Thr Gly Ala Tyr Lys Cys Phe Tyr Arg Glu Thr Asp Leu Ala Ser
            100                 105                 110
Val Ile Tyr Val Tyr Val Gln Asp Tyr Arg Ser Pro Phe Ile Ala Ser
        115                 120                 125
Val Ser Asp Gln His Gly Val Val Tyr Ile Thr Glu Asn Lys Asn Lys
    130                 135                 140
Thr Val Val Ile Pro Cys Leu Gly Ser Ile Ser Asn Leu Asn Val Ser
145                 150                 155                 160
Leu Cys Ala Arg Tyr Pro Glu Lys Arg Phe Val Pro Asp Gly Asn Arg
                165                 170                 175
Ile Ser Trp Asp Ser Lys Lys Gly Phe Thr Ile Pro Ser Tyr Met Ile
            180                 185                 190
Ser Tyr Ala Gly Met Val Phe Cys Glu Ala Lys Ile Asn Asp Glu Ser
        195                 200                 205
Tyr Gln Ser Ile Met Tyr Ile Val Val Val Gly Tyr Arg Ile Tyr
    210                 215                 220
Asp Val Val Leu Ser Pro Ser His Gly Ile Glu Leu Ser Val Gly Glu
225                 230                 235                 240
Lys Leu Val Leu Asn Cys Thr Ala Arg Thr Glu Leu Asn Val Gly Ile
                245                 250                 255
Asp Phe Asn Trp Glu Tyr Pro Ser Ser Lys His Gln His Lys Lys Leu
            260                 265                 270
Val Asn Arg Asp Leu Lys Thr Gln Ser Gly Ser Glu Met Lys Lys Phe
        275                 280                 285
Leu Ser Thr Leu Thr Ile Asp Gly Val Thr Arg Ser Asp Gln Gly Leu
    290                 295                 300
Tyr Thr Cys Ala Ala Ser Ser Gly Leu Met Thr Lys Lys Asn Ser Thr
305                 310                 315                 320
Phe Val Arg Val His Glu Lys Pro Phe Val Ala Phe Gly Ser Gly Met
                325                 330                 335
Glu Ser Leu Val Glu Ala Thr Val Gly Glu Arg Val Arg Ile Pro Ala
            340                 345                 350
Lys Tyr Leu Gly Tyr Pro Pro Pro Glu Ile Lys Trp Tyr Lys Asn Gly
        355                 360                 365
Ile Pro Leu Glu Ser Asn His Thr Ile Lys Ala Gly His Val Leu Thr
    370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
            420                 425                 430
Asp Ser Tyr Gln Tyr Gly Thr Thr Gln Thr Leu Thr Cys Thr Val Tyr
        435                 440                 445
Ala Ile Pro Pro Pro His His Ile His Trp Tyr Trp Gln Leu Glu Glu
    450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
```

-continued

```
                500             505             510
Thr Val Ser Thr Leu Val Ile Gln Ala Ala Asn Val Ser Ala Leu Tyr
            515                 520                 525
Lys Cys Glu Ala Val Asn Lys Val Gly Arg Gly Glu Arg Val Ile Ser
            530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
                580                 585                 590
Ile His Val Gly Glu Leu Pro Thr Pro Val Cys Lys Asn Leu Asp Thr
                595                 600                 605
Leu Trp Lys Leu Asn Ala Thr Met Phe Ser Asn Ser Thr Asn Asp Ile
            610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
                660                 665                 670
Leu Glu Asn Gln Thr Thr Ser Ile Gly Glu Ser Ile Glu Val Ser Cys
            675                 680                 685
Thr Ala Ser Gly Asn Pro Pro Pro Gln Ile Met Trp Phe Lys Asp Asn
            690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Gly Leu Tyr Thr
                725                 730                 735
Cys Gln Ala Cys Ser Val Leu Gly Cys Ala Lys Val Glu Ala Phe Phe
                740                 745                 750
Ile Ile Glu Gly Ala Gln Glu Lys Thr Asn Leu Glu Ile Ile Ile Leu
            755                 760                 765
Val Gly Thr Ala Val Ile Ala Met Phe Phe Trp Leu Leu Leu Val Ile
            770                 775                 780
Ile Leu Arg Thr Val Lys Arg Ala Asn Gly Gly Glu Leu Lys Thr Gly
785                 790                 795                 800
Tyr Leu Ser Ile Val Met Asp Pro Asp Glu Leu Pro Leu Asp Glu His
                805                 810                 815
Cys Glu Arg Leu Pro Tyr Asp Ala Ser Lys Trp Glu Phe Pro Arg Asp
                820                 825                 830
Arg Leu Lys Leu Gly Lys Pro Leu Gly Arg Gly Ala Phe Gly Gln Val
            835                 840                 845
Ile Glu Ala Asp Ala Phe Gly Ile Asp Lys Thr Ala Thr Cys Arg Thr
            850                 855                 860
Val Ala Val Lys Met Leu Lys Glu Gly Ala Thr His Ser Glu His Arg
865                 870                 875                 880
Ala Leu Met Ser Glu Leu Lys Ile Leu Ile His Ile Gly His His Leu
                885                 890                 895
Asn Val Val Asn Leu Leu Gly Ala Cys Thr Lys Pro Gly Gly Pro Leu
                900                 905                 910
Met Val Ile Val Glu Phe Cys Lys Phe Gly Asn Leu Ser Thr Tyr Leu
            915                 920                 925
```

-continued

Arg Ser Lys Arg Asn Glu Phe Val Pro Tyr Lys Thr Lys Gly Ala Arg
            930                 935                 940
Phe Arg Gln Gly Lys Asp Tyr Val Gly Ala Ile Pro Val Asp Leu Lys
945                 950                 955                 960
Arg Arg Leu Asp Ser Ile Thr Ser Ser Gln Ser Ser Ala Ser Ser Gly
                965                 970                 975
Phe Val Glu Glu Lys Ser Leu Ser Asp Val Glu Glu Glu Ala Pro
            980                 985                 990
Glu Asp Leu Tyr Lys Asp Phe Leu Thr Leu Glu His Leu Ile Cys Tyr
            995                 1000                1005
Ser Phe Gln Val Ala Lys Gly Met Glu Phe Leu Ala Ser Arg Lys
    1010                1015                1020
Cys Ile His Arg Asp Leu Ala Ala Arg Asn Ile Leu Leu Ser Glu
    1025                1030                1035
Lys Asn Val Val Lys Ile Cys Asp Phe Gly Leu Ala Arg Asp Ile
    1040                1045                1050
Tyr Lys Asp Pro Asp Tyr Val Arg Lys Gly Asp Ala Arg Leu Pro
    1055                1060                1065
Leu Lys Trp Met Ala Pro Glu Thr Ile Phe Asp Arg Val Tyr Thr
    1070                1075                1080
Ile Gln Ser Asp Val Trp Ser Phe Gly Val Leu Leu Trp Glu Ile
    1085                1090                1095
Phe Ser Leu Gly Ala Ser Pro Tyr Pro Gly Val Lys Ile Asp Glu
    1100                1105                1110
Glu Phe Cys Arg Arg Leu Lys Glu Gly Thr Arg Met Arg Ala Pro
    1115                1120                1125
Asp Tyr Thr Thr Pro Glu Met Tyr Gln Thr Met Leu Asp Cys Trp
    1130                1135                1140
His Gly Glu Pro Ser Gln Arg Pro Thr Phe Ser Glu Leu Val Glu
    1145                1150                1155
His Leu Gly Asn Leu Leu Gln Ala Asn Ala Gln Gln Asp Gly Lys
    1160                1165                1170
Asp Tyr Ile Val Leu Pro Ile Ser Glu Thr Leu Ser Met Glu Glu
    1175                1180                1185
Asp Ser Gly Leu Ser Leu Pro Thr Ser Pro Val Ser Cys Met Glu
    1190                1195                1200
Glu Glu Glu Val Cys Asp Pro Lys Phe His Tyr Asp Asn Thr Ala
    1205                1210                1215
Gly Ile Ser Gln Tyr Leu Gln Asn Ser Lys Arg Lys Ser Arg Pro
    1220                1225                1230
Val Ser Val Lys Thr Phe Glu Asp Ile Pro Leu Glu Glu Pro Glu
    1235                1240                1245
Val Lys Val Ile Pro Asp Asp Asn Gln Thr Asp Ser Gly Met Val
    1250                1255                1260
Leu Ala Ser Glu Glu Leu Lys Thr Leu Glu Asp Arg Thr Lys Leu
    1265                1270                1275
Ser Pro Ser Phe Gly Gly Met Val Pro Ser Lys Ser Arg Glu Ser
    1280                1285                1290
Val Ala Ser Glu Gly Ser Asn Gln Thr Ser Gly Tyr Gln Ser Gly
    1295                1300                1305
Tyr His Ser Asp Asp Thr Asp Thr Thr Val Tyr Ser Ser Glu Glu
    1310                1315                1320
Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350
Pro Pro Val
    1355

<210> SEQ ID NO 3
<211> LENGTH: 9
<212> TYPE: PRT
<213> ORGANISM: artificial sequence
<220> FEATURE:
<223> OTHER INFORMATION: synthetic peptide

<400> SEQUENCE: 3

Val Ile Leu Thr Asn Pro Ile Ser Met
1               5

<210> SEQ ID NO 4
<211> LENGTH: 10
<212> TYPE: PRT
<213> ORGANISM: artificial sequence
<220> FEATURE:
<223> OTHER INFORMATION: synthetic peptide

<400> SEQUENCE: 4

Phe Ser Asn Ser Thr Asn Asp Ile Leu Ile
1               5                   10

<210> SEQ ID NO 5
<211> LENGTH: 9
<212> TYPE: PRT
<213> ORGANISM: artificial sequence
<220> FEATURE:
<223> OTHER INFORMATION: synthetic peptide

<400> SEQUENCE: 5

Val Leu Leu Trp Glu Ile Phe Ser Leu
1               5

<210> SEQ ID NO 6
<211> LENGTH: 9
<212> TYPE: PRT
<213> ORGANISM: artificial sequence
<220> FEATURE:
<223> OTHER INFORMATION: synthetic peptide

<400> SEQUENCE: 6

Ala Leu Ile Glu Gly Lys Asn Lys Thr
1               5

<210> SEQ ID NO 7
<211> LENGTH: 9
<212> TYPE: PRT
<213> ORGANISM: artificial sequence
<220> FEATURE:
<223> OTHER INFORMATION: synthetic peptide

<400> SEQUENCE: 7

Ala Met Phe Phe Trp Leu Leu Leu Val
1               5

<210> SEQ ID NO 8
<211> LENGTH: 9
<212> TYPE: PRT
<213> ORGANISM: artificial sequence
<220> FEATURE:
<223> OTHER INFORMATION: synthetic peptide

```
<400> SEQUENCE: 8

Val Leu Leu Ala Val Ala Leu Trp Leu
1               5

<210> SEQ ID NO 9
<211> LENGTH: 10
<212> TYPE: PRT
<213> ORGANISM: artificial sequence
<220> FEATURE:
<223> OTHER INFORMATION: synthetic peptide

<400> SEQUENCE: 9

Leu Met Thr Lys Lys Asn Ser Thr Phe Val
1               5                   10

<210> SEQ ID NO 10
<211> LENGTH: 10
<212> TYPE: PRT
<213> ORGANISM: artificial sequence
<220> FEATURE:
<223> OTHER INFORMATION: synthetic peptide

<400> SEQUENCE: 10

Phe Leu Ser Thr Leu Thr Ile Asp Gly Val
1               5                   10

<210> SEQ ID NO 11
<211> LENGTH: 10
<212> TYPE: PRT
<213> ORGANISM: artificial sequence
<220> FEATURE:
<223> OTHER INFORMATION: synthetic peptide

<400> SEQUENCE: 11

Trp Leu Leu Leu Val Ile Ile Leu Arg Thr
1               5                   10

<210> SEQ ID NO 12
<211> LENGTH: 9
<212> TYPE: PRT
<213> ORGANISM: artificial sequence
<220> FEATURE:
<223> OTHER INFORMATION: synthetic peptide

<400> SEQUENCE: 12

Val Ile Ala Met Phe Phe Trp Leu Leu
1               5

<210> SEQ ID NO 13
<211> LENGTH: 10
<212> TYPE: PRT
<213> ORGANISM: artificial sequence
<220> FEATURE:
<223> OTHER INFORMATION: synthetic peptide

<400> SEQUENCE: 13

Leu Leu Ser Glu Lys Asn Val Val Lys Ile
1               5                   10
```

PEPTIDE EPITOPES OF VEGFR-2/KDR THAT INHIBIT ANGIOGENESIS

CROSS REFERENCE TO RELATED APPLICATION

This is a continuation of U.S. patent application Ser. No. 11/404,555, filed on Apr. 14, 2006, now abandoned which in turn claims the benefit of U.S. provisional application 60/671,867, filed on Apr. 15, 2005. Both of the prior applications are incorporated herein by reference in their entirety.

FIELD

This disclosure relates to cancer immunotherapy. More specifically, this disclosure relates to the use of immunogenic peptides of the Vascular Endothelial Growth Factor Receptor 2 to elicit an anti-angiogenic immune response useful for the treatment of cancer.

BACKGROUND

Angiogenesis, the formation of new capillary blood vessels, is essential for the growth and metastasis of solid tumors. The Vascular Endothelial Growth Factor (VEGF) family of proteins is one of the most potent and specific positive regulators of angiogenesis. These proteins bind to three tyrosine-kinase receptors, VEGFR-1 (Vascular Endothelial Growth Factor Receptor 1/Flt-1), VEGFR-2 (KDR/Fetal liver kinase 1, Flk-1) and VEGFR-3 (Flt-4). Neuropilin-1 is the fourth receptor that can bind specifically one of the VEGF isoforms: (VEGF165) and enhances its binding to VEGFR-1 (Soker et al., *Cell* 92(6):735-45, 1998). In general, VEGFR-1 and VEGFR-2/KDR are expressed on vascular endothelial cells whereas VEGFR-3 is expressed on lymphatic endothelial cells (Partanen et al., Cancer 86:2406, 1999; Kaipainen et al., *Proc Natl Acad Sci USA* 92:3566-70, 1995).

VEGFR-2/KDR is a major mediator of the mitogenic, angiogenic and permeability-enhancing effects of VEGF (Ferrara et al., *Nat. Med.* 9(6):669-676, 2003), and VEGFR-2/KDR is involved in the process of vascularization and angiogenesis. For example VEGFR-2/KDR-null mice die in utero between days 8.5 and 9.5 without any sign of vasculogenesis or organized blood vessels (Shalaby et al. *Nature* 376:62-66, 1995), demonstrating that VEGFR-2/KDR has an important role in the process of vascularization and angiogenesis.

VEGFR-2/KDR is highly expressed in tumor associated endothelial cells and contributes to tumor growth, invasion and metastasis (Dias et al., *J Clin Invest.* 106(4):511-521, 2000; Santos et al., *Blood* 103(10):3883-3889, 2004; St. Croix et al., *Science* 289:1197-1202, 2000). In addition, VEGFR-2/KDR is also expressed on the surface of several tumor cells including: B cell lymphoma and leukemia, multiple myeloma, urothelial bladder cancer, breast cancer, and lung cancer, among others (El-Obeid et al., *Leuk Res.* 28(2):133-137, 2004; Kumar et al., *Leukemia* 17(10):2025-2031, 2003; Gakiopoulou-Givalou et al., *Histopathology* 43(3):272-279, 2003; Kranz et al., *Int J Cancer* 84(3):293-298, 1999; Decaussin et al., *J Pathol.* 188(4):369-377, 1999). The relatively high level of expression on tumor cells relative to normal vascular endothelial cells suggests that VEGFR-2/KDR is a suitable target of tumor therapy.

Anti-angiogenic strategies targeting VEGFR-2/KDR have long been sought. Small molecule tyrosine kinase inhibitors targeting VEGFR-2/KDR, such as SU5416 have been shown to be effective in treating certain types of carcinomas in vitro and in vivo (Fong et al., *Cancer Res.* 59(1):99-106, 1999; Zangari et al., *Clin Cancer Res.* 10(1 Pt 1):88-95, 2004). Monoclonal antibodies against VEGFR-2/KDR can inhibit tumor angiogenesis and growth of several human and murine tumors (Prewett et al., *Cancer Res.* 59(20):5209-5218, 1999; Zhu et al., *Cancer Res.* 58(15):3209-3214, 1998). Wei et al., have shown that specific immune responses can be induced by xenogeneic endothelial cells and can protect mice from tumor challenge (Wei et al., *Nat. Med.* (10):1160-1166, 2000). Vaccine strategies against VEGFR-2/KDR have also been attempted. Tumor growth can be successfully inhibited by immunotherapy targeting VEGFR-2/KDR through a DNA vaccine encoding the full-length VEGFR-2/KDR (Niethammer et al., *Nat Med* 8:1369-1375, 2002), or dendritic cells transfected with a full-length VEGFR-2/KDR encoding construct (Nair et al., *Blood* 102(3):964-971, 2003), or pulsed with recombinant full-length VEGFR-2/KDR protein (Li et al., *J. Exp. Med.* 195(12):1575-1584, 2002). Some of these strategies have attributed the anti-tumor effects elicited to CD8+CTLs (Wei et al., *Nat. Med.* (10): 1160-1166, 2000; Niethammer et al., *Nat Med* 8:1369-1375, 2002; Yiwen et al., *J. Exp. Med.* 195:1575-1584, 2002), indicating that CTLs elicited by immunization against VEGFR-2/KDR can destroy endothelial cells derived from tumor associated vessels. To date, no human or murine VEGFR-2/KDR CTL epitopes have been identified.

The present disclosure provides murine and human MHC Class I epitopes of VEGFR-2/KDR, and demonstrates their efficacy as an anti-angiogenic vaccine.

SUMMARY OF THE DISCLOSURE

The present disclosure provides antigenic peptides of Vascular Endothelial Growth Factor Receptor 2(VEGFR-2)/KDR. The antigenic VEGFR-2/KDR peptides bind MHC Class I proteins and can elicit an anti-angiogenic immune response following administration to a subject. Pharmaceutical compositions including the peptides and/or antigen presenting cells that exhibit the VEGFR-2/KDR peptides on their cell surface are also described. Methods for eliciting an immune response and methods for inhibiting angiogenesis by administering such pharmaceutical compositions are also disclosed.

The foregoing and other features and advantages of the invention will become more apparent from the following detailed description of a several embodiments which proceeds with reference to the accompanying figures.

(experimental release−spontaneous release)/(maximum release−spontaneous release)×100.

Upper panel: effector cells from mice immunized with KDR2, Lower panel: effectors from KDR3 immunized mice.

Figure 5A:
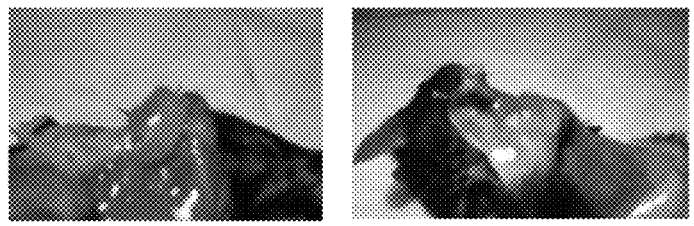
Figure 5B:
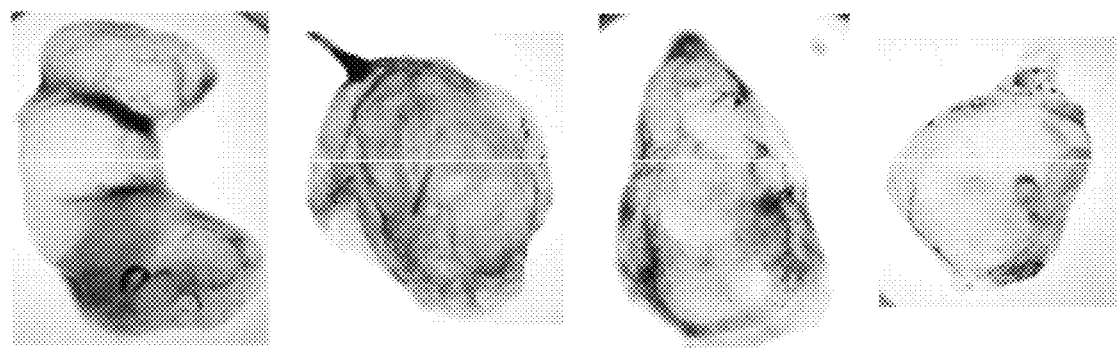
Figure 5C:
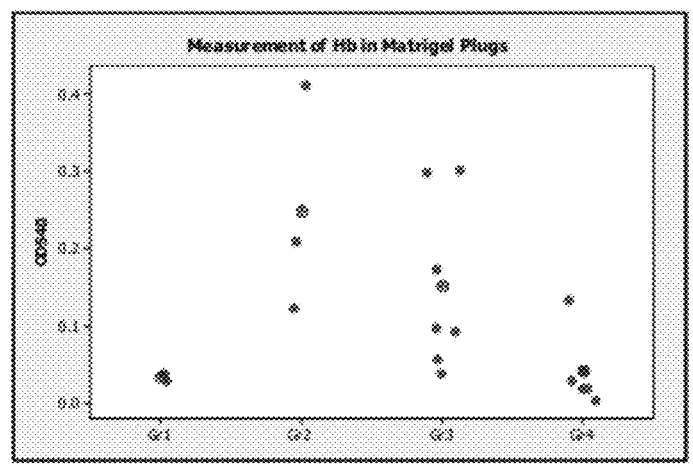

FIGS. 5A-C illustrate the results of a Matrigel Plug Assay illustrating that angiogenesis can be inhibited by peptide immunization. Mice (C57BL/6) were immunized three times with 4 weeks interval in the tails. 10 days after the last immunization, mice were injected subcutaneously (right flanks) with 500 µl of a solution containing Matrigel, with or without 100 ng/ml murine VEGF. Plugs were resected after 10 days and were shaken overnight in 2 volumes water before 1 hr of incubation with an equal volume of Drabkin reagent (Sigma) and colorimetric assessment at A540. FIG. 5A. illustrates representative digital images before the Matrigel Plugs were resected: Left: plug with muVEGF in mice immunized with IFA+GM-CSF+aCD40; Right: plug with muVEGF in mice immunized with IFA+GM-CSF+aCD40+KDR2+KDR3. FIG. 5B illustrates representative digital images of the Matrigel Plugs: (a): plug without mu-VEGF as negative control; (b): plug with mu-VEGF as positive control; (c) IFA+GM-CSF+anti-CD40; (d) IFA+GM-CSF+anti-CD40+KDR2+KDR3. FIG. 5C. is a graph indicating hemoglobin content in the Matrigel plugs by Drabkin reagent. Gr1: negative control, plugs without muVEGF (n=2); Gr2: positive control, plugs with muVEGF (n=3); Gr3: plugs with muVEGF from mice immunized with IFA+GM-CSF+aCD40 (n=7); Gr4: plugs with muVEGF from mice immunized with IFA+GM-CSF+ aCD40+KDR2+KDR3 (n=6). *P<0.05 relative to Gr3 by Student's t-test. ⚹ indicates mean of the group.

Figure 6:
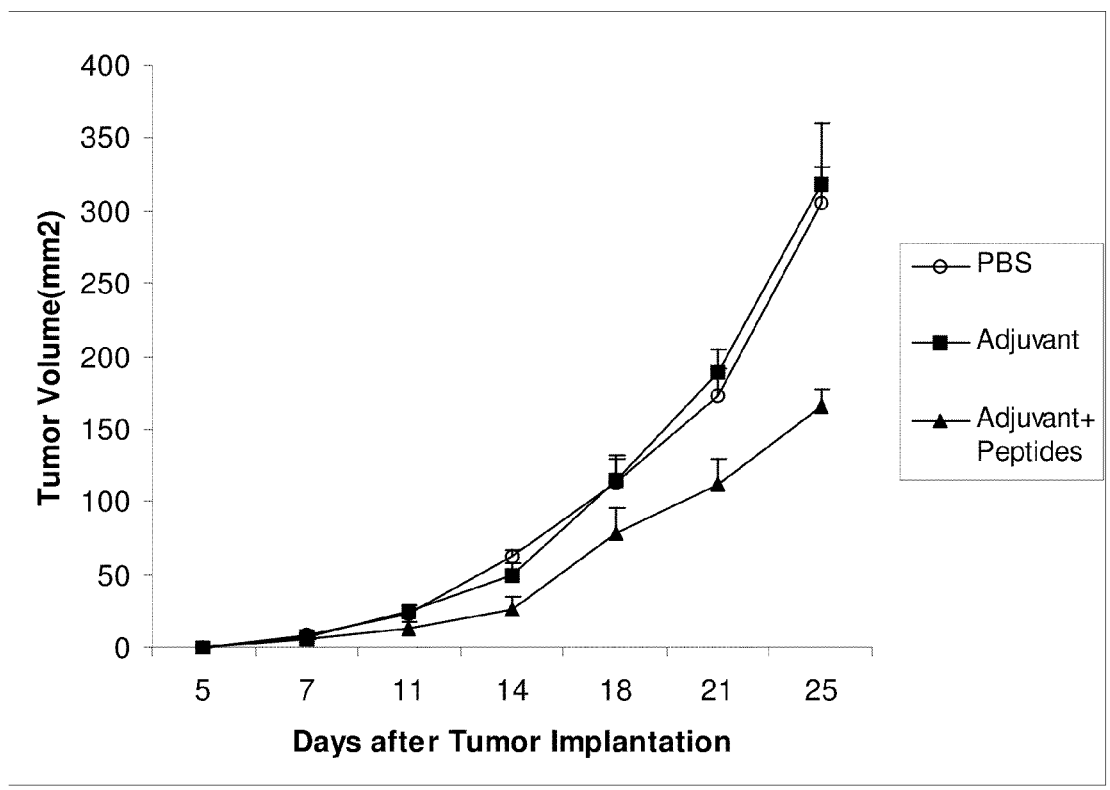

FIG. 6 is a line graph illustrating inhibition of MC-38 tumor growth by KDR2 and KDR3 immunization. 3×10$^4$ MC38 colon cancer cells were injected s.c. into the right flanks of C57BL/6 mice at day 1, Mice were randomized into 3 groups (5 mice each) at day 5 were immunized with PBS, adjuvants only or adjuvants plus 100 µg KDR2 and KDR3 peptides. Tumors were measured by caliper twice a week till mice were sacrificed when tumor reach 2 millimeter in length. Error bars indicate standard deviation. ○ mice injected with PBS served as control; ■ mice immunized with IFA+GM-CSF+anti-CD40; ▲ mice vaccinated with IFA+GM-CSF+anti-CD40+KDR2+KDR3. The results shown that vaccination with KDR2 and KDR3 can inhibit MC38 tumor growth.

Figure 7:
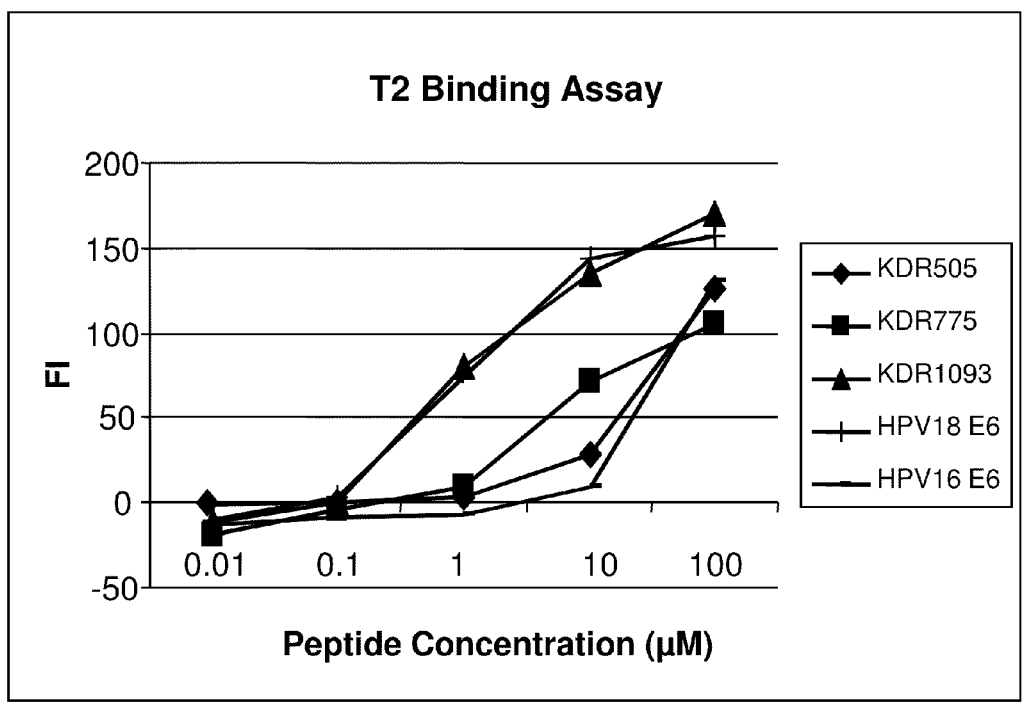

FIG. 7 is a line graph illustrating binding of exemplary human VEGFR-2/KDR peptides to HLA-A2 in a T2 binding assay.

Figure 8A:
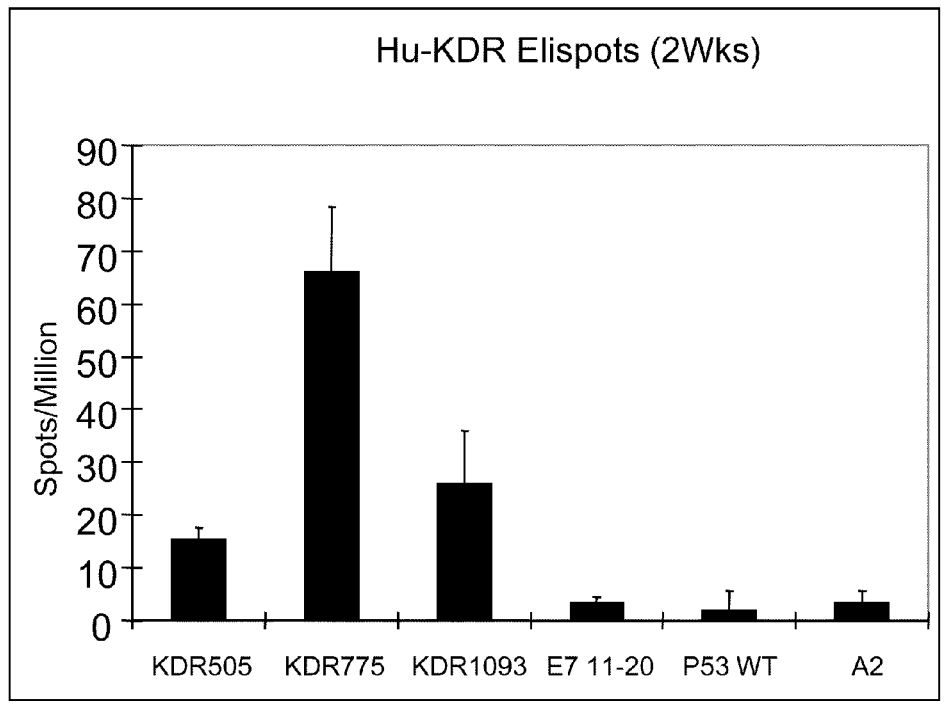
Figure 8B:
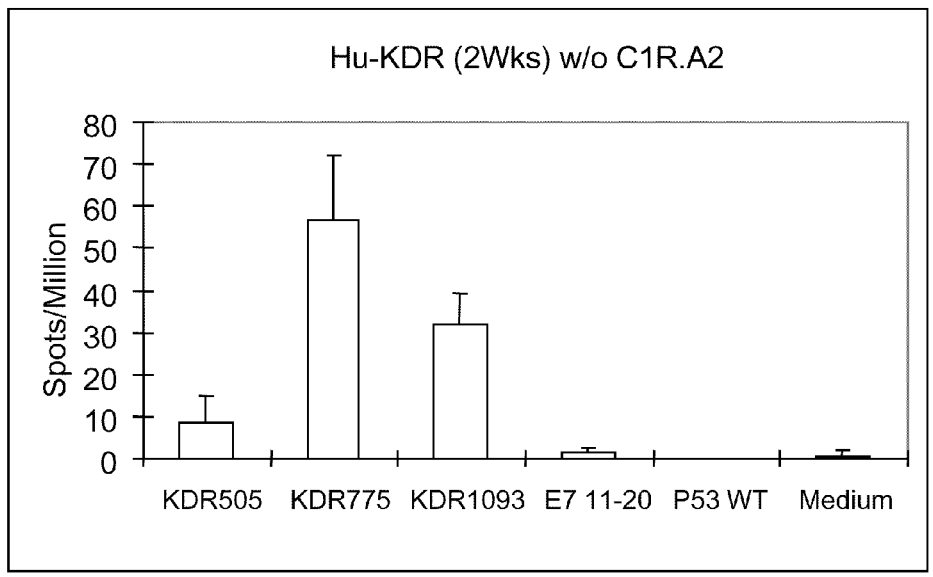

FIGS. 8A and B are bar graphs illustrating production of IFN-γ secreting T cells in response to immunization with exemplary human VEGFR-2/KDR peptides (KDR505, KDR775 and KDR1093). (A) and (B) illustrate the production of IFN-γ secreting T cells stimulated in the presence and absence of C1R.A2 cells, respectively.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO:1 is the amino acid sequence of the murine VEGFR-2/KDR.

SEQ ID NO:2 is the amino acid sequence of the human VEGFR-2/Flk-1.

SEQ ID NO:3 is the amino acid sequence of the peptide (murine) KDR2.

SEQ ID NO:4 is the amino acid sequence of the peptide (murine) KDR3.

SEQ ID NO:5 is the amino acid sequence of a human VEGFR-2/KDR peptide.

SEQ ID NO:6 is the amino acid sequence of a human VEGFR-2/KDR peptide.

SEQ ID NO:7 is the amino acid sequence of a human VEGFR-2/KDR peptide.

SEQ ID NO:8 is the amino acid sequence of a human VEGFR-2/KDR peptide.

SEQ ID NO:9 is the amino acid sequence of a human VEGFR-2/KDR peptide.

SEQ ID NO: 10 is the amino acid sequence of a human VEGFR-2/KDR peptide.

SEQ ID NO: 11 is the amino acid sequence of a human VEGFR-2/KDR peptide.

SEQ ID NO: 12 is the amino acid sequence of a human VEGFR-2/KDR peptide.

SEQ ID NO:13 is the amino acid sequence of the peptide (murine) KDR1.

DETAILED DESCRIPTION

I. Introduction

Vascular Endothelial Growth Factor (VEGF) is an important regulator of angiogenesis, including neovascularization of tumors. The present disclosure provides peptide epitopes of the VEGFR-2/KDR receptor which are useful as immunogenic compositions to elicit an immune response that targets VEGFR-2/KDR expressing cells, such as cells of tumor vascular endothelia. Because VEGFR-2/KDR is highly expressed on the surface of endothelial cells undergoing abnormal angiogenesis associated with tumor progression as compared to normal vascular endothelial cells, such a targeted immune response is an effective means of reducing tumor growth in vivo, either as an independent therapy or in conjunction with surgical resection and/or chemotherapy.

Targeting tumor vascular endothelia provides several advantages as compared to targeting tumor cells directly. For example, MHC molecules on the surface of endothelial cells are not down-regulated as are MHC molecules on tumor cells. Effector cells (such as T cells) and/or antibodies can reach endothelial cell targets more easily (via the vasculature) than these effectors can reach tumor cells. Because each blood vessel supplies hundreds (or more) of tumor cells, targeting blood vessels efficiently targets numerous tumor cells. In addition, treatment targeted against endothelial cells is not limited on tumor type or tissue, and is likely to impact at least four different types of cells: tumor associated endothelial cells expressing VEGFR-2/KDR, tumor cells expressing VEGFR-2/KDR, circulating endothelial progenitors (CEPs, CD34+AC133+VEGFR-2/KDR+)(Yu et al., *Blood* 103: 1373-1375, 2004) and circulating endothelial cells (CECs, CD45-VEGFR-2/KDR+)(Schuh et al., *Cancer Res.* 63:8345-8350, 2003). Thus, therapies targeting the blood vessels that supply tumors are likely to be more efficient and effective than targeting the tumor cells themselves.

To date, all of the attempts to elicit a therapeutically relevant immune response against VEGFR-2/KDR have used full-length protein. Compared to immunotherapies involving full-length protein, peptide vaccine is much easier to synthesize, and can be produced at significantly lower cost. The high purity of peptide vaccine is another advantage because peptide vaccines do not have any of the potential dangers associated with infection by recombinant viruses or allergy due to an exogenous protein in the vaccine composition. The present disclosure provides novel CD8+ T cell epitopes from VEGFR-2/KDR, and demonstrates their efficacy as an anti-angiogenic tumor therapy.

A first aspect of the present disclosure relates to peptides that bind to a Major Histocompatibility (MHC) Class I molecule. These peptides are chains of amino acids (between 3 and 30 amino acids in length) that are subsequences of the Vascular Endothelial Growth Factor Receptor 2 (VEGFR-2/KDR). Typically, the VEGFR-2/KDR MHC Class I binding peptides are at least 8 amino acids, and no more than 12 amino acids in length. Usually, the peptides consist of a subsequence of VEGFR-2/KDR of 9 amino acids or 10 amino acids in length.

In one embodiment, the peptides are subsequences of the murine (mouse) VEGFR-2/KDR. More particularly, the peptides are subsequences of the murine VEGFR-2/KDR that include the sequence T-N-X-I (TNXI), where X is any amino acid. For example, the sequences VILTNPISM (KDR2: SEQ ID NO:3) and FSNSTNDILI (KDR3: SEQ ID NO:4) are peptide subsequences of the murine VEGFR-2/KDR that bind murine MHC Class I molecules (H-2D$^b$) and elicit an anti-angiogenic immune response following administration to a subject. Alternatively, the peptides include at least one amino acid addition, deletion or substitution relative to SEQ ID NO:3 or SEQ ID NO:4. In embodiments including one or more amino acid deletion, addition or substitution, the peptides nonetheless retain the ability to bind MHC Class I and to elicit an anti-angiogenic immune response.

In another embodiment, the peptide is a subsequence of a human VEGFR-2/KDR. The peptides include the motif: X-L/M-(X)$_{5 \text{ or } 6}$-L/T/F/G, where X is any amino acid. Thus, the peptide includes any amino acid at position one (with respect to the N-terminus of the peptide), a leucine or methionine at position two, any amino acid at positions three through seven or eight, and a leucine, threonine, phenylalanine or glycine at position eight or nine. For example, VLLWEIFSL (SEQ ID NO:5), ALIEGKNKT (SEQ ID NO:6), AMFFWLLLV (SEQ ID NO:7), VLLAVALWL (SEQ ID NO:8), LMTKKNSTFV (SEQ ID NO:9), FLSTLTIDGV (SEQ ID NO: 10), and WLLLVIILRT (SEQ ID NO: 11) are exemplary human VEGFR-2/KDR peptides that bind MHC Class I (e.g., HLA-A2) and elicit an anti-angiogenic immune response following administration to a subject. The peptides can optionally include one or more amino acid addition, deletion or substitution that does not impair the peptide's ability to bind MHC Class I or substantially alter its antigenicity.

Typically, the anti-angiogenic immune response involves a cytotoxic (CTL) response specific for cells that express VEGFR-2/KDR. Such a response involves the proliferation and activation of CD8+ T cells with T cell receptors (TCRs) that specifically bind to or interact with an epitope of VEGFR-2/KDR. In some cases, the immune response also results in the production of antibodies that bind specifically to VEGFR-2/KDR.

Another aspect of the disclosure relates to isolated antigen presenting cells (APCs) that present the VEGFR-2/KDR peptides on a cell surface MHC Class I molecule. The APCs include dendritic cells, macrophages and B cells. In some embodiments, the APCs are human APCs, such as human dendritic cells. In some embodiments, the APC is contacted with at least one VEGFR-2/KDR peptide by exposing the external surface of the APC to the VEGFR-2/KDR peptide(s), e.g., by culturing the APC in a medium containing the VEGFR-2/KDR peptide(s).

Another aspect of the disclosure relates to pharmaceutical compositions (medicaments) including the VEGFR-2/KDR peptides or APCs (such as autologous APCs) that present the peptides on cell surface MHC Class I molecules, and a pharmaceutically acceptable carrier or excipient. For example, the pharmaceutical compositions described herein are immunogenic compositions. That is, the pharmaceutical compositions or medicaments can be used to elicit an immune response in a subject. The immune response typically involves the proliferation and activation of T cells that have a TCR that binds to an epitope of VEGFR-2/KDR. The immune response can include a cytotoxic T cell (CTL) response that targets endothelial cells involved in tumor angiogenesis. Methods for producing the medicaments are also disclosed.

The disclosure also provides methods for eliciting an immune response against a VEGFR-2/KDR. Such an immune response is specific for an antigen expressed on vascular endothelial cells. Such methods involve administering an immunologically effective amount of a pharmaceutical composition that includes at least one VEGFR-2/KDR peptide as described herein, or at least one APC that presents such a peptide. The immune responses elicited following administration of an immunologically effective amount of these pharmaceutical compositions reduces or inhibits angiogenesis (that is, the immune response is an anti-angiogenic immune response). For example, the immune response can inhibit or reduce tumor associated angiogenesis or neovascularization associated with cancer. Thus, the immune response inhibits or reduces angiogenesis associated with tumor progression, metastasis and/or vascularization associated with regrowth of a tumor following surgical resection or chemotherapy. Accordingly, the pharmaceutical compositions described herein can be administered to a subject with a tumor, e.g., to inhibit vascularization of the tumor, to inhibit growth or progression of the tumor, to inhibit metastasis by the tumor, etc. In some cases, the subject is a human subject. Optionally, the pharmaceutical composition includes or is administered in combination with a cytokine, an immunostimulatory agent (such as an adjuvant) or a chemotherapeutic agent.

Additional technical details are provided under the specific topic headings below.

II. Abbreviations

APC: antigen presenting cell
CEC; CEP: circulating endothelial cell; circulating endothelial progenitor
CTL: cytotoxic T lymphocyte
DC: dendritic cell
FACS: Fluorescence Activated Cell Sorting (or scanning)
FBS: Fetal Bovine Serum
GM-CSF: granulocyte/macrophage colony stimulating factor
H-2: murine (mouse) major histocompatibility complex
HLA: human major histocompatibility complex
IFA: Freund's incomplete adjuvant
IFN-γ: Gamma interferon
MHC: Major Histocompatibility Complex
PBL: peripheral blood lymphocytes
PBMC: peripheral blood mononuclear cells
PBS: Phosphate buffered saline
TCR: T cell receptor
μM: micromolar
VEGF: Vascular Endothelial Growth Factor
VEGFR-2/VEGFR-2/KDR/Flk-1: VEGF Receptor 2

II. Terms

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of specific terms are provided:

Adjuvant: A vehicle used to enhance antigenicity; such as a suspension of minerals (alum, aluminum hydroxide, or aluminum phosphate) on which antigen is adsorbed; or water-in-oil (MF-59; Freund's incomplete adjuvant) emulsion in which antigen solution is emulsified in mineral oil, sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199).

Anchor Amino Acid Residue or Anchor Residue: Binding of a peptide epitope to an MHC molecule is determined in significant part by the presence of anchor amino acid residues that correspond to the recognition motif or "anchor motif" of the MHC molecule.

Antigen: A compound, composition, or substance that can stimulate the production of antibodies or a T cell response in an animal, including compositions that are injected or absorbed into an animal. An antigen interacts with one or more products of specific humoral or cellular immunity. "Epitope" or "antigenic determinant" refers to a site on an antigen to which B cells (or antibodies) and/or T cells bind. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. In some cases, T cells bind to the epitope, when the epitope is bound to an MHC molecule. An epitope can be as few as three amino acids. More commonly, an epitope is composed of at least about 7 amino acids. For example, an epitope presented in the context of an MHC molecule is usually at least 8 amino acids in length. Usually such an epitope is no longer than about 12 amino acids. For example, an epitope presented by an MHC Class I molecule is typically about 9, or about 10 amino acids in length. Thus, the epitopes presented by MHC molecules are typically peptides.

Antigen Presenting Cell (APC): Antigen presenting cells are cells that can process antigens and display the antigen peptide fragments on the cell surface together with molecules involved in lymphocyte activation. Antigen presenting cells include dendritic cells (DCs), macrophages, and B cells.

Antibody: Immunoglobulin molecules and immunologically active portions of immunoglobulin molecules, that is, molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. As used herein, the term antibody also includes recombinant antibodies produced by expression of a nucleic acid that encodes one or more antibody chains in a cell (e.g., see U.S. Pat. No. 4,745,055; U.S. Pat. No. 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984).

The term antibody also includes an antigen binding fragment of a naturally occurring or recombinant antibody. Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., *Nature* 341:544-546, 1989) which consists of a $V_H$ domain; (v) an isolated complementarity determining region (CDR); and (vi) a F(ab')$_2$ fragment, a bivalent fragment comprising two Fab fragments linked by a disulfide bridge at the hinge region.

Cancer: A malignant neoplasm that has undergone characteristic anaplasia with loss of differentiation, increased rate of growth, invasion of surrounding tissue, and is capable of metastasis. Residual cancer is cancer that remains in a subject after any form of treatment given to the subject to reduce or eradicate cancer. Metastatic cancer is a cancer at one or more sites in the body other than the site of origin of the original (primary) cancer from which the metastatic cancer is derived.

Chemotherapy; chemotherapeutic agents: As used herein, any chemical agent with therapeutic usefulness in the treatment of diseases characterized by abnormal cell growth. Such diseases include tumors, neoplasms and cancer as well as diseases characterized by hyperplastic growth such as psoriasis. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g., see, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The immunogenic VEGFR-2/KDR peptides disclosed herein can be used in conjunction with additional chemotherapeutic agents.

Dendritic cell (DC): Dendritic cells are the principal antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells.

Epitope: An antigenic determinant. An epitope is the particular chemical groups or peptide sequences on a molecule that are antigenic, that is, that elicit a specific immune response. An antibody specifically binds a particular antigenic epitope, e.g., on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell (or humoral immune) response, and results in the production of specific antibodies, that is, an antibody response.

Immunologically effective amount: An immunologically effective amount of an antigen is an amount which elicits an immune response following administration to a subject. For example, a prophylactically effective amount, e.g., of a vaccine, elicits a protective immune response that prevents or inhibits at least one symptom of a disease upon administration to a subject. A therapeutically effective amount elicits an immune response that reduces at least one symptom of a disease or ameliorates at least one condition associated with a disease. For example, administration of a therapeutically effective amount of a VEGFR-2/KDR peptide is sufficient to elicit an immune response that reduces, inhibits or prevents formation of blood vessels associated with tumor progression or metastasis.

Inhibiting or treating a disease: Inhibiting a disease, such as tumor growth, refers to inhibiting the full development of a disease or to reducing or inhibiting a symptom of the disease. "Treatment" refers to a therapeutic or prophylactic intervention that ameliorates a sign or symptom of a disease or pathological condition related to the disease, such as the tumor.

Isolated: An "isolated" biological component (such as a protein) has been substantially separated or purified away from other biological components in the cell of the organism in which the component naturally occurs, i.e., chromosomal and extra-chromosomal DNA and RNA, other proteins and organelles. Proteins and peptides that have been "isolated" include proteins and peptides purified by standard purification methods. The term also includes proteins and peptides prepared by recombinant expression in a host cell, as well as chemically synthesized proteins and peptides.

Lymphocytes: A type of white blood cell that is involved in the immune defenses of the body. There are two main types of lymphocytes: B cells and T cells.

Major Histocompatibility (MHC) molecule: The Major Histocompatibility molecules are proteins encoded by polymorphic genes located on human chromosome 6 (HLA loci) and mouse chromosome 13 (H-2 loci) that present antigens to T cells, e.g., on the surface of antigen presenting cells. T cells expressing CD8 interact with peptides presented by MHC Class I molecules, whereas T cells expressing CD4 interact with peptides presented by MHC Class II molecules.

Mammal: This term includes both human and non-human mammals. Similarly, the term "subject" includes both human and veterinary subjects.

Neoplasm: An abnormal cellular proliferation, which includes benign and malignant tumors, as well as other proliferative disorders.

Peptide: A chain of amino acids of between 3 and 30 amino acids in length, (a chain of two amino acids is typically referred to as a dipeptide). More commonly, a peptide is between 5 and 25 amino acids (e.g., between 7 and 15 amino acids). For example, a peptide can be at least 5 amino acids, or at least about 7 amino acids, or 8 amino acids, or 9 amino acids, or 10 amino acids, or up to about 12 amino acids, e.g., 11 amino acids, 12 amino acids or 13 amino acids.

Protein Purification: Protein purification is the process by which naturally occurring or synthetic polypeptides are isolated from the materials with which they were associated during synthesis. Similarly, purification of a peptide is the process by which a peptide is isolated from the materials with which it was associated during synthesis, e.g., artificially synthesized or enzymatically produced by digestion of a polypeptide. The VEGFR-2/KDR peptides disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Prac-* tice, Springer Verlag, New York, 1982). Substantial purification denotes purification from other cellular or synthetic components. A substantially purified protein is at least about 60%, 70%, 80%, 90%, 95%, 98% or 99% pure. Thus, in one specific, non-limiting example, a substantially purified peptide is 90% free of other synthetic components.

Purified: The term purified does not require absolute purity; rather, it is intended as a relative term. Thus, for example, a purified peptide is one in which the peptide is more enriched than the peptide upon completion of artificial synthesis. In one embodiment, a preparation is purified such that the peptide represents at least about 60% (such as, but not limited to, 70%, 80%, 90%, 95%, 98% or 99%) of the total peptide or content of the preparation.

Subject: Living multi-cellular vertebrate organisms, a category that includes both human and veterinary subjects, including human and non-human mammals.

Subsequence: A subsequence of a peptide, polypeptide or nucleic acid (polynucleotide) is any portion of the reference peptide, polypeptide or nucleic acid up to and including the entire reference molecule.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8 T cell is a cytotoxic T lymphocyte.

Immunogenic VEGFR-2 Peptides

Peptides corresponding to amino acid subsequences of Vascular Endothelial Growth Factor Receptor 2 (VEGFR-2)/KDR that include an antigenic epitope of the receptor, which binds to MHC Class I, can be used as vaccines to generate an immune response specific for VEGFR-2/KDR. These peptides are VEGFR-2/KDR immunogenic peptides. VEGFR-2/KDR immunogenic peptides include peptide subsequences of a mammalian VEGFR-2/KDR receptor. The murine (mouse) VEGFR-2/KDR sequence is represented by SEQ ID NO:1, and can be found in GENBANK® under accession no: P35918. The human VEGFR-2/KDR sequence is represented by SEQ ID NO:2, and can be found in GENBANK® under accession no: P35968. The mouse and human VEGFR-2/KDR receptors are members of a genus of orthologues, additional members of which can be identified by searching GENBANK® or other electronic sequence databases.

In some embodiments, the immune response produced following administration of VEGFR-2/KDR immunogenic peptides targets vascular endothelial cells that express VEGFR-2/KDR, and inhibits their proliferation. Because VEGFR-2/KDR is highly expressed by endothelial cells during angiogenesis associated with tumor progression and metastasis, the immune response produced following administration of the VEGFR-2/KDR peptides preferentially targets tumor associated angiogenesis.

Peptides presented in the context of MHC Class I molecules of an antigen presenting cell (APC) are bound by T cell receptors (TCRs) on the surface of CD8 expressing cells. Binding of the TCR in conjunction with the interaction of CD8 and MHC Class I initiates a signaling pathway that results in proliferation and activation of VEGFR-2/KDR specific cytotoxic T cells. These cytotoxic T cells subsequently bind to and kill target cells expressing VEGFR-2/KDR, inhibiting tumor associated angiogenesis. Thus, the disclosed VEGFR-2/KDR peptides can be used as therapeutically and/or prophylactically as vaccines to induce an anti-angiogenic immune response.

The amino acid sequence of the VEGFR-2/KDR peptides is such that it contains an amino acid motif involved in binding to a MHC Class I molecule. Such an amino acid motif can be referred to as a Class I binding "anchor motif." For example, the human Class I molecule HLA-A2 (0201) binds to the following anchor motif: $X[L/M]X_{5-7}[L/V]$. To simplify reference to amino acid sequences, the following conventions are employed throughout this specification. All amino acids are designated using International Union of Pure and Applied Chemistry-International Union of Biochemistry and Molecular Biology (IUPAC-IUB) nomenclature. Thus, X is any (unspecified) amino acid, L is leucine, M is methionine and V is valine. Where two amino acids are enclosed within brackets [ ], and/or separated by a solidus (/), either amino acid can be located at the specified position within the sequence. A numerical subscript indicates a specified plurality of residues, thus $X_5$ indicates five unspecified amino acids. $X_{5-7}$ indicates 5 or 6 or 7 unspecified amino acids. For convenience, the specified amino acids (indicated above within brackets), which are the predominant determinants of Class I binding are designated "anchor residues."

Immunogenic peptides can be identified using anchor motifs or other methods, such as neural net or polynomial determinations, known in the art, see, e.g., RANKPEP (available on the world wide web at: mif.dfci.harvard.edu/Tools/rankpep.html); ProPredI (available on the world wide web at: imtech.res.in/raghava/propredI/index.html); Bimas (available on the world wide web at: www-bimas.dcrt.nih.gov/molbi/hla_bind/index.html); and SYFPEITH (available on the world wide web at: syfpeithi.bmi-heidelberg.com/scripts/MHCServer.dll/home.htm). For example, algorithms are used to determine the "binding threshold" of peptides, and to select those with scores that give them a high probability of MHC or antibody binding at a certain affinity. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. Anchor residues are conserved residues that provide a contact point with the MHC molecule.

Immunogenic peptides can also be identified by measuring their binding to a specific MHC protein (e.g., HLA-A*0201) and by their ability to stimulate CD8+ T cells when presented in the context of the MHC protein.

Exemplary mouse VEGFR-2/KDR immunogenic peptides include VILTNPISM (KDR2: SEQ ID NO:3) and FSNSTNDILI (KDR3: SEQ ID NO:4). These exemplary peptides are indicative of a genus of MHC Class I binding peptides characterized by the internal consensus sequence "TNXI." As discussed below, substantially identical peptides that maintain the internal TNXI consensus sequence are also predicted to be immunogenic VEGFR-2/KDR peptides.

Exemplary human VEGFR-2/KDR immunogenic peptides include VLLWEIFSL (SEQ ID NO:5), ALIEGKNKT (SEQ ID NO:6), AMFFWLLLV (SEQ ID NO:7), VLLAVALWL (SEQ ID NO:8), LMTKKNSTFV (SEQ ID NO:9), FLSTLTIDGV (SEQ ID NO: 10), WLLLVIILRT (SEQ ID NO: 11). These immunogenic VEGFR-2/KDR peptides are representative of a genus of peptides that share a common MHC Class I anchor motif represented by the sequence:

X[L/M]X$_{5-7}$[L/V]. While these peptides share an anchor motif that is predictive of binding to the HLA-A*0201 allele, certain of these peptides will also bind to different HLA-A2 alleles and to different Class I molecules. These peptides can be determined according to the methods outlined above.

In addition to the exemplary peptides set forth in SEQ ID NOs:3-11, substantially identical peptides that include one or more amino acid additions, deletions or substitutions (with respect to any one of SEQ ID NOs:3-11), which maintain the capacity to bind to MHC Class I molecules, and which elicit an immune response involving T cells (and/or antibodies) that interact with VEGFR-2/KDR are also included among the immunogenic peptides of this disclosure.

A substantially identical peptide to one (or more than one) of SEQ ID NOs: 3-11 is a peptide that shares substantial sequence identity with the reference sequence. That is, the substantially identical peptide consists of predominantly identical amino acid residues. Sequence identity is frequently measured in terms of percentage identity (or similarity); the higher the percentage, the more similar the two sequences are. Variants of a VEGFR-2/KDR immunogenic peptide possess a high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

A substantially identical variant of a VEGFR-2/KDR immunogenic peptide is typically characterized by at least about 70%, for example at least about 80%, and usually at least about 90% or more, sequence identity counted over the entire peptide sequence. Such an alignment can be performed manually or with the assistance of a sequence alignment program such as BLAST. Thus, a substantially identical variant of one of SEQ ID NOs:3-11 can have one amino acid addition, deletion or substitution. Some substantially identical variants can have as many as two, and in some cases, as many as three, amino acid additions, deletions or substitution. Nonetheless, the peptides retain the MHC Class I binding and antigenic properties of the exemplary VEGFR-2/KDR immunogenic peptides. Methods for confirming MHC Class I binding properties, and antigenicity are described below, e.g., in the Examples section.

For example, a substantially identical variant of a VEGFR-2/KDR immunogenic peptide can have one, two (or as many as three) conservative amino acid substitutions. A "conservative" amino acid substitutions is a substitution that does not substantially reduce the ability of the peptide to bind MHC or alter the antigenicity of an epitope of VEGFR-2/KDR. Specific, non-limiting examples of conservative substitutions include the following examples provided in Table 1.

TABLE 1

Blosum similarity matrix

| Amino Acid | Conservative Substitutions |
|---|---|
| G | A, S, N |
| P | E |
| D | S, K, Q, H, N, E |
| E | P, D, S, R, K, Q, H. N |
| N | G, D, E, T, S, R, K, Q, H |
| H | D, E, N, M, R, Q |
| Q | D, E, N, H, M, S, R, K |
| K | D, E, N, Q, R |
| R | E, N, H, Q, K |
| S | G, D, E, N, Q, A, T |
| T | N, S, V, A |
| A | G, S, T, V |
| M | H, Q, Y, F, L, I, V |
| V | T, A, M, F, L, I |
| I | M, V, Y, F, L |
| L | M, V, I, Y, F |
| F | M, V, I, L, W, Y |
| Y | H, M, I, L, F, W |
| W | F, Y |
| C | None |

The term conservative variant also includes the use of a substituted amino acid in place of an unsubstituted parent amino acid, provided that antibodies raised to the substituted polypeptide also immunoreact with the unsubstituted polypeptide. Non-conservative substitutions are those that reduce MHC binding or antigenicity.

Typically, any amino acid substitutions in an VEGFR-2/KDR immunogenic peptide will occur in a position that is not involved in MHC Class I binding. Nonetheless, so long as the anchor motif is maintained, certain substitutions in the anchor residues are predicted to preserve MHC Class I binding. For example, substitution of leucine for methionine is a predicted conservative mutation in the context of an HLA-A2 binding peptide. Thus, a conservative variant of the peptide of SEQ ID NO:7 (AMFFWLLLV) can have a leucine substituted for methionine at amino acid position two. Similarly, a conservative variant of the peptide of SEQ ID NO:9 includes a peptide with a leucine substituted for methionine at position two. Likewise, a conservative variant of the peptide of SEQ ID NO:9 includes a peptide with a leucine substituted for phenylalanine at position nine. As indicated in these examples, a conservative variant can have a single substituted amino acid selected from groups of conservative amino acid substitutions given in Table 1. A conservative variant can sometimes include more than one amino acid substitution. For example, a conservative variant of SEQ ID NO:9 can include two amino acid substitutions such as a leucine for methionine substitution at position two and a leucine for phenylalanine substitution at position nine. In all of the preceding examples, the substituted amino acid are designated, the remaining amino acids are identical to those of the reference peptide sequence. Conservative variants can also include one (or two, or rarely three) amino acid additions or deletions. Such additions or deletions can be at the ends of the peptide sequence, or can be internal, so long as the anchor residues are maintained. For example, the peptide sequence VIAMFFWLL (SEQ ID NO:12) is a variant that comprises a deletion of two amino acids at one end and a concomitant addition of two amino acids at the other end, relative to AMFFWLLLV (SEQ ID NO:7), maintains the anchor residues, and thus, is substantially similar to the peptide of SEQ ID NO:7.

Any of the peptides described above can be produced by well-known chemical synthesis methods. Chemical synthesis of peptides is described in the following publications: S. B. H. Kent, Biomedical Polymers, eds. Goldberg and Nakajima, Academic Press, New York, pp. 213-242, 1980; Mitchell et al., J. Org. Chem., 43, 2845-2852, 1978; Tam, et al., Tet. Letters, 4033-4036, 1979; Mojsov, A. R. Mitchell, and R. B. Merrifield, J. Org. Chem., 45, 555-560, 1980; Tam et al., Tet. Letters, 2851-2854, 1981; and Kent et al., Proceedings of the IV International Symposium on Methods of Protein Sequence Analysis, (Brookhaven Press, Brookhaven, N.Y., 1981. Alternatively, the peptides can be produced using recombinant nucleic acid technology, for example, by expressing recombinant nucleic acids that encode a fusion protein including the desired peptide. Following expression in a suitable cell line, the peptide can be isolated and cleaved from the fusion protein.

In addition to the VEGFR-2/KDR peptides of SEQ ID NOs:3-11, analogs (non-peptide organic molecules), derivatives (chemically functionalized peptide molecules obtained starting with the disclosed peptide sequences) and variants (homologs) of these peptides can be utilized in the methods described herein. Each peptide of this disclosure is comprised of a sequence of amino acids, which can be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic variants include compounds in which the three-dimensional arrangement of the chemical constituents of such peptido- and organomimetics mimics the three-dimensional arrangement of the peptide backbone and component amino acid side chains of a VEGFR-2/KDR immunogenic peptide. These are peptido- and organomimetics of an immunogenic VEGFR-2/KDR, and can have measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

The ability of any of the above described peptides to bind MHC Class I can be confirmed using assays available in the art. For example, the ability of a murine VEGFR-2/KDR peptide to bind a mouse Class I molecule, such as H-2 Db can be determined in a MHC stabilization assay employing RMA-S cells as described in Lyman et al., *J. Virol.* 76:3125-3134, 2002, and in the EXAMPLES Section below. The ability of a human VEGFR-2/KDR peptide to bind a human Class I molecule, such as an HLA-A2 protein can be evaluated in a T2 MHC binding assay as described by Cerundolo et al., *Nature* 342:449-452, 1990. In brief, T2 cells are cultured in RPMI1640 with 10% FBS, and grown in 5% $CO_2$ at 37° C. Cells ($1 \times 10^5$) in a volume of 100 µl of RPMI 1640 (serum free) are aliquoted into 96-well, U-bottomed plates and incubated with peptide at a final concentration of 0.1-100 µM plus 5 nM $\beta_2$ microglobulin (Cymbus Biotechnology Ltd., Chandlers Ford, Hampshire, United Kingdom) for 18 h at 37° C. in 5% $CO_2$. The level of stabilized HLA-A2 on the surface of the T2 cells is detected using the pan HLA class I monoclonal antibody W6/32 (European Collection of Animal Cell Cultures (ECACC), Porton Down, Salisbury) that recognizes stabilized HLA-A2 complexes. The primary monoclonal antibody can be labeled or can be detected using, e.g., a labeled goat antimouse IgG (Cambridge Biosciences, Cambridge, United Kingdom) as the second layer. Samples are fixed in 1% paraformaldehyde in PBS prior to analysis and analyzed on a Becton Dickinson FACSCAN®.

The ability of a specific peptide to elicit an immune response can be confirmed as described in the EXAMPLES. For example, the ability of a peptide to stimulate the production of interferon-γ (IFNγ) producing CTL can be evaluated using an IFN-Elispot assay, which measures the frequency of IFN producing T cells that respond to the peptide. Appropriate mouse (as described in the Materials and Methods section) or human cells are used to present the peptide. Following co-culture with splenocytes or peripheral blood cells, IFNγ producing cells are quantitated. Confirmation that the IFNγ response is due to CD8+ CTL specific for the peptide can be obtained using a MHC Class I tetramer assay, as described below.

In addition, the ability of the peptide elicited immune response to inhibit angiogenesis can be ascertained using a Matrigel plug assay. Details of the assay are provided below in the Materials and Methods Section. This assay can be adapted to evaluate human peptides simply by conducting the assay in a transgenic mouse that expresses human HLA-A2 and human VEGFR-2/KDR.

The ability of the peptide elicited immune response to inhibit angiogenesis can also be evaluated in vivo, in a wound healing assay. Two weeks after the vaccination with peptide (s), transgenic mice carrying a human HLA A2 transgene and wild type (C57BL/6) control mice are subject to punch biopsy under general anesthetic (ketamine/xylazine, 75/10 mg/kg IP). One or more circular wounds of approximately 3-mm diameter are inflicted on the dorsal area using a sterile biopsy punch instrument. Typically multiple wounds (for example, four) are inflicted on each animal to increase observation points and reduce the number of animals required. Time until wound closure is then evaluated.

Immunogenic Compositions

The VEGFR-2/KDR immunogenic peptides disclosed herein can be administered to a subject to elicit an immune response. Such an immune response can be a therapeutic (including a prophylactic immune response), in particular, an anti-angiogenic and/or anti-tumor immune response. An immune response elicited by administration of the VEGFR-2/KDR immunogenic peptide(s) typically includes a T cell response, e.g., a cytotoxic T cell response that targets cells expressing VEGFR-2/KDR. Accordingly, methods for making a medicament or pharmaceutical composition containing the VEGFR-2/KDR peptides described above are included herein. The pharmaceutical compositions (medicaments) include at least one isolated or synthetic MHC Class I-binding peptide that includes a subsequence of VEGFR-2/KDR or one or more isolated antigen presenting cells (APCs) that present the VEGFR-2/KDR peptides on a cell surface MHC Class I molecule, in a pharmaceutically acceptable carrier or excipient.

In certain embodiments, the pharmaceutical compositions include the peptides represented by SEQ ID NO:3 and/or SEQ ID NO:4, or substantially identical peptides, as described above.

In other embodiments, the pharmaceutical compositions (medicaments) include one or more human VEGFR-2/KDR peptides. For example, a pharmaceutical composition can contain an immunologically effective amount of a human VEGFR-2/KDR peptide that is capable of binding to a human MHC Class I protein and eliciting an immune response. An immunogenic composition can thus include, an immunologically effective amount of any of the peptides VLLWEIFSL (SEQ ID NO:5), ALIEGKNKT (SEQ ID NO:6), AMFF-WLLLV (SEQ ID NO:7), VLLAVALWL (SEQ ID NO:8), LMTKKNSTFV (SEQ ID NO:9), FLSTLTIDGV (SEQ ID NO: 10), or WLLLVIILRT (SEQ ID NO: 11). Alternatively, an immunogenic composition can include a combination of VEGFR-2/KDR peptides (for example, a plurality of SEQ ID NOs: 5, 6, 7, 8, 9, 10 and/or 11), in any combination. For example, in one specific embodiment, the composition contains a combination of the following peptides: VLLWEIFSL (SEQ ID NO:5), ALIEGKNKT (SEQ ID NO:6), and AMFF-WLLLV (SEQ ID NO:7). Alternatively or additionally, the immunogenic compositions can include one or more substantially identical immunogenic peptide, which include one or a small number of amino acid additions, deletions or substitutions with respect to any of SEQ ID NOs:5-11.

In one specific, non-limiting example the pharmaceutical composition (medicament) includes about 0.1 µg to about 1,000 µg, for example, at least about 1 µg, or at least about 10 pg to about 100 µg, or to about 500 µg, of one or a plurality of selected VEGFR-2/KDR immunogenic peptides (e.g., SEQ ID NOs:3-11). The immunogenic TARP polypeptide can also be administered with agents that promote dendritic cell maturation. Specific, non-limiting examples of agents of use are interleukin-4 (IL-4) and granulocyte/macrophage colony stimulating factor (GM-CSF), or flt-3 ligand (flt-3L).

Typically, preparation of an pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for presentation of the peptides by antigen presenting cells.

Aqueous compositions typically include an effective amount of the peptide dispersed (for example, dissolved or suspended) in a pharmaceutically acceptable carrier or aqueous medium. The phrases "pharmaceutically acceptable" or "pharmacologically acceptable" refer to molecular entities and compositions that do not produce an adverse, allergic or other undesirable reaction when administered to a human or animal subject. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with production of an immune response by a VEGFR-2/KDR immunogenic peptide, its use in the immunogenic compositions is contemplated. Supplementary active ingredients also can be incorporated into the compositions. For example, certain pharmaceutical compositions can include the peptides in water, mixed with a suitable surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

Pharmaceutically acceptable carriers or excipients are known to those of ordinary skill in the described, e.g., in *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

For example, the pharmaceutical compositions (medicaments) can include one or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art.

In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, i.e., to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

An adjuvant can be included in the composition. In one embodiment, the adjuvant is a mixture of stabilizing detergents, micelle-forming agent, and oil available under the name Provax® (IDEC Pharmaceuticals, San Diego, Calif.). An adjuvant can also be an immunostimulatory nucleic acid, such as a nucleic acid including a CpG motif.

In other embodiments, the immunogenic compositions (medicaments) include antigen presenting cells (APCs), such as dendritic cells, which have been pulsed or co-incubated with one or more VEGFR-2/KDR immunogenic peptides in vitro. Typically, the APCs are in a suspension in a pharmaceutically acceptable carrier or medium, which preserves the viability and activity of the APCs. In one specific, non-limiting example, the antigen presenting cells can be autologous cells. A therapeutically effective amount of the antigen presenting cells can then be administered to a subject.

The VEGFR-2/KDR immunogenic peptide(s) can be delivered to the APCs or to APC precursors via any method known in the art, including, but not limited to, pulsing APCs directly with antigen. For example, human peripheral blood mononuclear cells can be separated from peripheral blood by centrifugation over Ficoll-Paque (Pharmacia, Uppsala, Sweden). Monocytes can be enriched by adherence to a plastic tissue culture flask for 90 minutes at 37° C. Adherent cells are then cultured for 7 days with 1000 units/ml GM-CSF and 1000 units/ml IL-4 in RPMI with 7% autologous serum. DCs are harvested with vigorous washing, and the DC phenotype is confirmed by flow cytometry using antibodies specific for CD14, CD80, CD86, MHC Class I and HLA-DR. DCs ($1\times10^6$/ml) are pulsed with 50 µg/ml of each peptide for 3 hours at room temperature in normal saline with 1% human albumin. Then, the DCs are washed twice and resuspended in normal saline with 1% human albumin before administration.

Alternatively, VEGFR-2/KDR peptides can be delivered to APCs utilizing a broad variety of antigen delivery vehicles, such as, for example, liposomes, or other vectors known to deliver antigen to cells.

Therapeutic Methods

The pharmaceutical compositions (medicaments) can be prepared for use in therapeutic (including prophylactic) regimens (e.g., vaccines) and administered to human or non-human subjects to elicit an immune response against one or more VEGFR-2/KDR epitopes. For example, the compositions described herein can be administered to a human (or non-human) subject to inhibit angiogenesis and/or to inhibit the growth, progression or metastasis of a tumor. Thus, the pharmaceutical compositions described above can be administered to a subject to elicit an anti-angiogenic or anti-tumor immune response. In other embodiments, the pharmaceutical compositions are administered to inhibit (treat) an autoimmune condition or disease characterized by or involving neovascularization. Such autoimmune disorders include, for example, rheumatoid arthritis, diabetes, systemic lupus erythematosus (e.g., chorioretinal neovascularization), psoriatic arthritis, psoriasis, and other inflammatory diseases of the skin. To elicit an immune response, a therapeutically effective (e.g., immunologically effective) amount of the VEGFR-2/KDR peptide(s) or a therapeutically effective amount of the APCs that present the VEGFR-2/KDR peptide(s) are administered to a subject, such as a human (or non-human) subject.

A "therapeutically effective amount" is a quantity of a chemical composition or a cell to achieve a desired effect in a subject being treated. For instance, this can be the amount necessary to inhibit tumor growth or to measurably alter outward symptoms of the tumor. In the context of an autoimmune disorder, a therapeutically effective amount is an amount that produces an observable improvement in at least one symptom of the disorder, such as joint tenderness, swelling, pain, loss of mobility, etc., in the case of rheumatoid arthritis. When administered to a subject, a dosage will generally be used that will achieve target tissue concentrations (for example, in lymphocytes) that is empirically determined to achieve an in vitro effect. Such dosages can be determined without undue experimentation by those of ordinary skill in the art.

In exemplary applications, compositions are administered to a patient suffering from a disease, such as a cancer or an autoimmune disease, in an amount sufficient to raise an immune response against VEGFR-2/KDR-expressing cells. Administration induces a sufficient immune response to slow the proliferation of such cells or to inhibit their growth, thereby inhibiting angiogenesis and/or reducing a sign or a symptom of the tumor. Amounts effective for this use will depend upon the severity of the disease, the general state of the patient's health, and the robustness of the patient's immune system. A therapeutically effective amount of the compound is that which provides either subjective relief of a symptom(s) or an objectively identifiable improvement as noted by the clinician or other qualified observer.

A pharmaceutical composition including a VEGFR-2/KDR immunogenic peptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated. In one embodiment, administration is by subcutaneous or intramuscular injection. To extend the time during which the peptide or protein is available to stimulate a response, the peptide can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

In one specific, non-limiting example, one or more VEGFR-2/KDR peptides are administered to elicit a cellular immune response (e.g., a cytotoxic T lymphocyte (CTL) response). A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinly-seryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

In an embodiment, in conjunction with the production of a CTL response to a VEGFR-2/KDR, a MHC Class II-restricted T-helper epitope is added along with the Class I restricted VEGFR-2/KDR immunogenic peptide to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see, Chesnut et al., "Design and Testing of Peptide-Based Cytotoxic T-Cell-Mediated Immunotherapeutics to Treat Infectious Diseases and Cancer," in Powell et al., eds., *Vaccine Design, the Subunit and Adjuvant Approach*, Plenum Press, New York, 1995).

In one specific, non-limiting example, about 0.1 μg to 10 mg of VEGFR2/KDR immunogenic peptide(s) are administered per subject per day. Dosages from 0.1 μg up to about 100 μg per subject per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Phamaceutical Sciences*, 19$^{th}$ Ed., Mack Publishing Company, Easton, Pa., 1995.

The compositions can be administered for therapeutic treatments. In therapeutic applications, a therapeutically effective amount of the composition is administered to a subject suffering from a disease, such as a cancer or an autoimmune disorder. Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see, Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

In some embodiments, mature antigen presenting cells (APCs) are generated to present the VEGFR-2/KDR immunogenic peptide(s). Most commonly, the APCs are dendritic cells (DCs), e.g., autologous DCs generated following isolation of peripheral blood mononuclear cells from the subject's blood. The DCs are loaded (e.g., pulsed) with one or more VEGFR-2/KDR immunogenic peptides and administered to a subject (for example, a subject with a tumor). The DCs are administered alone or in conjunction with one or more adjuvants, immunostimulatory agents, cytokines and/or chemotherapeutic agents. The specific regimen can involve administration of the various agents simultaneously or in separate pharmaceutical compositions to be delivered at the same or different times.

Alternatively, the APCs are used to sensitize CD8+ cells (e.g., CTLs), such as tumor infiltrating lymphocytes (TILs) from the target tumor or peripheral blood lymphocytes (PBLs). The TILs or PBLs can be from the subject to be treated (autologous). Alternatively, the TILs or PBLs can be from another subject (heterologous). However, where heterologous cells are used, they should at least be MHC Class-I restricted to the HLA haplotype of the subject. An effective amount of the sensitized cells are then administered to the subject.

Peripheral blood or bone marrow can be used as the source of responder cells (e.g., CTL precursors). The appropriate antigen-presenting cells are incubated with VEGFR-2/KDR peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived, such as VEGFR-2/KDR (e.g. SEQ ID NO: 2). The sensitized CD8+ cells can be administered to a subject to inhibit tumor associated angiogenesis and tumor growth.

In cell based applications, a therapeutically effective amount of activated antigen presenting cells, or activated lymphocytes, are administered to a subject suffering from a disease, e.g., a primary or metastatic tumor, in an amount sufficient to raise an immune response to VEGFR-2/KDR-expressing vascular endothelial cells. The resulting immune response is sufficient to slow the proliferation of such cells or to inhibit their growth, thereby inhibiting angiogenesis, or to reduce a sign or a symptom of the tumor.

In some embodiments, the effect of any of the pharmaceutical compositions can be augmented by administering one or more cytokines, such as IL-2, IL-3, IL-6, IL-10, IL-12, IL-15, IL-18, and/or interferons. Generally, the cytokine is selected to not promote angiogenesis, or is administered in a concentration that does not promote angiogenesis. Thus, for example, while GM-CSF is favorably employed to stimulate proliferation and differentiation of APC in vitro, it is less desirable to administer GM-CSF. In some case, cytokines with demonstrated anti-angiogenic effects, such as IL-12 and/or IL-18 are included in the pharmaceutical compositions or administered in a separate formulation in conjunction with the immunogenic compositions described above.

In certain embodiments, any of these immunotherapies is augmented by administering an additional chemotherapeutic agent. In one example, this administration is sequential (e.g., to prevent or reduce interference with proliferation or survival of APCs and/or T cells). Examples of such agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocortical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Reagents for Detecting T-Cells that Specifically Bind VEGFR-2/KDR

Reagents are provided herein for the detection of CD8 expressing cells that specifically bind VEGFR-2/KDR. These reagents are complexes made up of tetrameric MHC Class I bound to VEGFR-2/KDR immunogenic peptides.

In some embodiments, the tetrameric MHC Class I complexes include mouse MHC Class I proteins in conjunction with mouse VEGFR-2/KDR immunogenic peptides. Such mouse complexes are particularly useful for detecting or identifying mouse CD8+ T cells (such as cytotoxic T cells) specific for VEGFR-2/KDR. For example, the MHC Class I tetrameric complexes can include a mouse VEGFR-2/KDR peptide that includes the internal sequence T-N-X-I (SEQ ID NO: 14). In specific embodiments, the tetrameric MHC Class I complexes include the peptide VILTNPISM or FSNSTNDILI. For example, the mouse tetrameric MHC Class I complexes can include the peptide VILTNPISM and/or the peptide FSNSTNDILI in conjunction with H-2 $D^b$ molecules.

In other embodiments, the tetrameric complexes include human VEGFR-2/KDR immunogenic peptides in conjunction with human MHC Class I proteins. These tetrameric MHC Class I complexes are useful for the detection of CD8+ T cells that specifically bind to the human VEGFR-2/KDR. For example, the complexes described herein including human VEGFR-2/KDR immunogenic peptides bound to human MHC Class I molecules can be used to detect or identify cytotoxic CD8+ T cells specific for VEGFR-2/KDR. For example, the immunogenic peptides are subsequences of human VEGFR-2/KDR that include the sequence X-L/M-$(X)_{5\,or\,6}$-L/T/F/G (SEQ ID NO: 15). In specific embodiments, the tetrameric complexes include the peptides VLLWEIFSL (SEQ ID NO:5), ALIEGKNKT (SEQ ID NO:6), AMFFWLLLV (SEQ ID NO:7), VLLAVALWL (SEQ ID NO:8), LMTKKNSTFV (SEQ ID NO:9), FLSTLTIDGV (SEQ ID NO: 10) and/or WLLVIILRT (SEQ ID NO: 11), respectively. For example, the tetrameric MHC Class I complex can include any of the aforementioned peptides bound to HLA-A2 molecules.

Tetrameric MHC Class I/peptide complexes can be synthesized using methods well known in the art (Altmann et al., *Science* 274:94, 1996, which is herein incorporated by reference). In one specific non-limiting example, purified HLA heavy chain and β2-microglobulin (β2m) can be synthesized by means of a prokaryotic expression system. One specific, non-limiting example of an expression system of use is the pET system (R&D Systems, Minneapolis, Minn.). The heavy chain is modified by deletion of the trans-membrane and cytosolic tail and COOH-terminal addition of a sequence containing the biotin protein ligase (Bir-A) enzymatic biotinylation site. Heavy chain, β2m, and peptide are then refolded. The refolded product can be isolated by any means known in the art, and then biotinylated by Bir-A. A tetramer is then produced by contacting the biotinylated product with streptavidin.

In one embodiment, the streptavidin is labeled. Suitable labels include, but are not limited to, enzymes, magnetic beads, colloidal magnetic beads, haptens, fluorochromes, metal compounds, radioactive compounds or drugs. The enzymes that can be conjugated to streptavidin include, but are not limited to, alkaline phosphatase, peroxidase, urease and β-galactosidase. The fluorochromes that can be conjugated to the streptavidin include, but are not limited to, fluorescein isothiocyanate, tetramethylrhodamine isothiocyanate, phycoerythrin, allophycocyanins and Texas Red. For additional fluorochromes that can be conjugated to streptavidin, see Haugland, R. P., *Molecular Probes: Handbook of Fluorescent Probes and Research Chemicals* (1992-1994). The metal compounds that can be conjugated to the streptavidin include, but are not limited to, ferritin, colloidal gold, and particularly, colloidal superparamagnetic beads. The haptens that can be conjugated to the streptavidin include, but are not limited to, biotin, digoxigenin, oxazalone, and nitrophenol. The radioactive compounds that can be conjugated to streptavidin are known to the art, and include but are not limited to technetium 99m ($^{99}$Tc), $^{125}$I and amino acids comprising any radionuclides, including, but not limited to, $^{14}$C, $^{3}$H and $^{35}$S. Generally, streptavidin labeled with a fluorochrome is utilized in the methods disclosed herein.

In one embodiment, a suspension of cells to be assayed for the presence of T cells that specifically bind to VEGFR-2/KDR is produced, and the cells are reacted with the tetramer in suspension. In one embodiment, these reagents are used to label cells, which are then analyzed by fluorescence activated cell sorting (FACS). A machine for FACS employs a plurality of color channels, low angle and obtuse light-scattering detection channels, and impedance channels, among other more sophisticated levels of detection, to separate or sort cells. Any FACS technique can be employed as long as it is not detrimental to the detection of the desired cells. (For exemplary methods of FACS see U.S. Pat. No. 5,061,620.)

T cells, for example, cytotoxic T cells identified using these tetrameric VEGFR-2/KDR-MHC Class I complexes can be expanded in vitro and autologously transfused or adoptively transferred to provide anti-angiogenic activity in vivo.

The disclosure is illustrated by the following non-limiting Examples.

EXAMPLES

Example 1

Growth of Cell Lines in Culture

The RMA-S(H-2b), EL4 (H-2b) and T2 cell lines were maintained in RPMI 1640 supplemented with 10% fetal calf serum, glutamine-pyruvate, and antibiotics in 5% CO2 at 37° C. Mouse endothelial cell line H5V (H-2b), bEND3(H-2d) and mouse colon cancer cell line MC38(H-2b) were maintained in DMEM supplemented with 10% fetal calf serum, glutamine-pyruvate, and antibiotics. Mouse epithelial cell line TC-1 (HPV16 E6 and E7 positive) was from ATCC. H5V and bEND3 cells were obtained from Dr. Yiwen Li (Wei et al., *Nat. Med.* 6:1160-1166, 2000). RMA-S cell line was obtained from Dr. Altan-Bonnet, Gregoire (NIH/NIAID).

Example 2

Prediction and Synthesis of Murine VEGFR-2 Peptides

The sequence of mouse VEGFR-2/KDR was evaluated using computer algorithms to identify H-2 Db binding epitopes. Two algorithms were employed to predict the epitope candidates binding to H-2 Db molecule: Bimas (on the world wide web at the bimas website) and SYFPEITH (on the world wide web at the syfpeithi website).

Three murine H-2 Db epitopes were identified. Three peptides, designated as VEGFR-2/KDR1, KDR2 and KDR3 respectively were predicted to bind the H-2 Db molecules by both computer programs: Bimas and SYFPEITH. The sequences of these peptides are shown in Table 2.

TABLE 2

Murine VEGFR-2/KDR immunogenic peptides

| Peptide | SEQ ID NO: | Sequence | Location | Bimas Score | SYFPEITH Score |
|---|---|---|---|---|---|
| KDR1 | SEQ ID NO: 13 | LLSEKNVVKI | 1033-1042 | 240.000 | 13 |
| KDR2 | SEQ ID NO: 3 | VILTNPISM | 400-408 | 660.000 | 24 |
| KDR3 | SEQ ID NO: 4 | FSNSTNDILI | 615-624 | 286.000 | 16 |

Peptides were synthesized using a commercial service (Sigma, The Woodlands, Tex.). Two peptides with known high binding affinity to H-2 Db and HLA-A2, Human Papilloma Virus (HPV) 16E7 49-57 (Feltkamp et al., *Eur. J. Immunol.* 23:2242-2249, 1993) and Human P53 264-272 (Theobald et al., *J. Exp. Med.* 185:833-841, 1997) served as positive and negative control respectively.

Example 3

Mouse VEGFR-2/KDR Peptides Bind H-2 Db

To test the binding affinity of these peptides to H-2 Db, an RMA-S binding experiment was performed, and the FI value in the assay was measured. Incubation of RMA-S cells with H-2 Db- or H-2 Kb-binding peptides has been shown to enhance surface expression of the respective MHC class I molecules on these cells by stabilizing the peptide-MHC complex (Ljunggren et al., *Nature* 346:476-480, 1990). The RMA-Binding assays were performed as previously described (Lyman et al., *J. Virol.* 76:3125-3134, 2002). Briefly, synthetic peptides were dissolved in dimethyl sulfoxide before dilution. For MHC-binding assays, RMA-S cells were loaded with various peptides for 16 to 18 h at 37° C. Levels of surface class I molecules were assessed by flow cytometric analysis (FACScan; Becton Dickinson) using mouse monoclonal antibodies specific for H-2 Db (Southern Biotech, clone No. 28-14-8). FI=Fluorescence after peptides stimulation/Fluorescence without peptide-1.

Previous data have shown that the HPV16E7 49-57 can bind to H-2 Db molecules efficiently and induce a strong CTL response in B6 mice (Feltkamp et al., *Eur. J. Immunol.*

23:2242-2249, 1993). HPV16E7 49-57 peptide was used as a positive control; and the human P53 264-272, known to bind HLA-A2 but not H-2 Db, was used as a negative control (FIG. 1).

Figure 1:
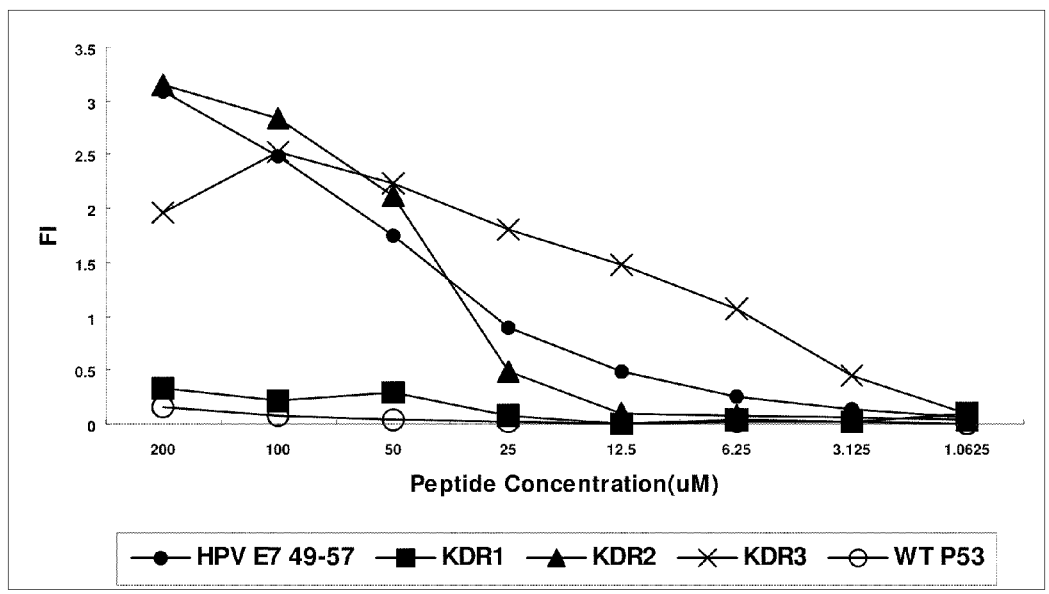
FIG. 1 is a line graph illustrating results of an RMA-S binding assay. KDR2 and KDR3 bind efficiently to H-2 Db molecules. RMA-S cells were loaded with various peptides for 16 to 18 h at 37° C. Levels of surface class I molecules were assessed by flow cytometric analysis using mouse monoclonal antibodies specific for H-2 Db. FI=Fluoresce measurement after peptides stimulation/Fluoresce measurement without peptide-1.: KDR1, ▲: KDR2, : KDR3, ○: wild type P53 264-272, : HPV 16 E7 49-57. HPV E7 49-57 and Human P53 264-272 serve as positive and negative control respectively. The results shown here are representative of three separate experiments.

As shown in FIG. 1, KDR2 and KDR3 peptides bind well to H-2 Db. Concentration of HPV16E7 49-57 at FI=0.5 was about 12.5 μM, while FI of the negative control, P53 264-272 could not reach 0.5 even at concentration of 200 μM, indicating that this peptide does not bind H-2 Db molecule and confirming that the assay was indicative of H-2 Db binding. FI of KDR3 was 0.5 when the concentration was about 3 μM, that for KDR2 was about 24 μM, suggested the binding affinity of KDR3 to H-2 Db was higher than KDR2 and the positive control, HPV16E7 49-57.

Example 4

VEGFR-2/KDR Peptides are Immunogenic

The immunogenicity of KDR2 and KDR3 was demonstrated in vivo by immunizing mice with the peptides and evaluating the resulting antigen specific immune response. Mice were immunized with selected peptide, together with murine GM-CSF and anti-mouse CD40 as adjuvants. An emulsion containing 50 μl Incomplete Freud's Adjuvants (IFA, Sigma) with or without 100 ng of peptide and 5 μg murine GM-CSF (Pepro Tech), 20 μg anti-murine CD40 monoclonal antibody (Southern Biotech, Clone number 1C10) was prepared in a final volume of 100 μl. Subcutaneous injections were performed on the tails of the mice with 1 ml syringes and 30 gauge needles. For the Matrigel Plug Assay, two boosts were injected at 4 week intervals.

IFN-γ Elispots assay was performed on draining lymph nodes cells (DLN) or splenocytes collected 2 weeks after vaccination to evaluate the antigen specific immune response against the VEGFR-2/KDR peptides. Elispot plates (Millipore, Bedford, Mass.) were coated with 8 μg of anti-gamma interferon (IFN-γ) antibody per ml in sterile phosphate-buffered saline (PBS) overnight at 4° C. Plates were washed and then blocked with RPMI 1640 with 10% FBS. Fresh splenocytes or cells after 1 week in vitro restimulation were used as effectors. 1 or $5 \times 10^5$ effector cells were co-cultured overnight with or without $2 \times 10^5$ irradiated (3,000 rads) EL4 cells in 200 μl media at 37° C., 5% CO2 in the presence of appropriate concentration of peptide. When H5V and bEND3 cells instead of EL4 were used as stimulators, they were treated with 0.1 mg/ml mitomycin C (Sigma, St. Louis) for half an hour at 37° C., then wash three times with PBS. $5 \times 10^4$ H5V or bEND3 cells were co-cultured overnight with $2 \times 10^5$ draining lymph nodes cells. Spots were developed as previously described using biotin-conjugated anti-cytokine antibodies (Endogen, Boston, Mass.) and streptavidin-horseradish peroxidase in 1% BSA-PBS.

Figure 2A:
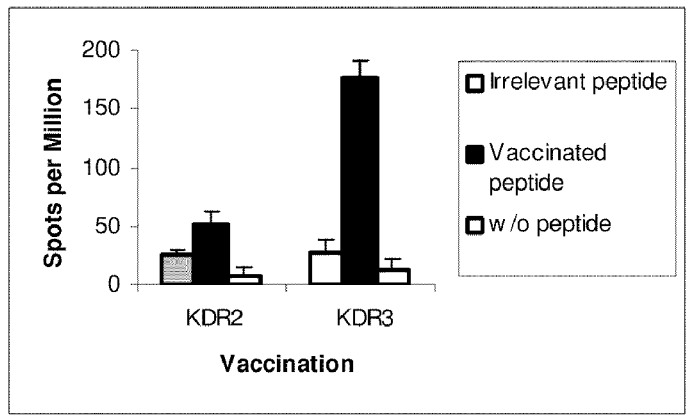
FIGS. 2A-C are bar graphs representing the results of IFN-Eli spot assays. Four groups of mice (5 mice per group) were vaccinated with different peptides (KDR1, KDR2, KDR3). Mice were sacrificed, spleen or drained lymph nodes (DLN) cells prepared as described in methods section served as effectors. Syngeneic EL4 cells (3,000 rads) pulsed with peptides or H5V cells after treated with MMC served as stimulators. Irradiated EL4 without peptide or MMC treated allogeneic bEND3 cells as control. Dot bar: EL4 pulsed with irrelevant peptide as negative control; Solid bar: EL4 pulsed with KDR2 or KDR3 respectively; Open bar: EL4 without any peptide; A. Results of fresh spleen cells; B. Results of spleen cells after 1 week restimulation in vitro; C. Cells from fresh drained lymph nodes stimulated with H5V or bEND3 cells.

The number of IFN-γ secreting fresh spleen cells after pulsing with KDR3 peptide was 176 and was about 6 times of that pulsed with irrelevant HPV E7 peptide (FIG. 2A). The number of IFN-γ secreting fresh spleen cells after KDR2 vaccination was about 50 times greater than background.

Figure 2B:
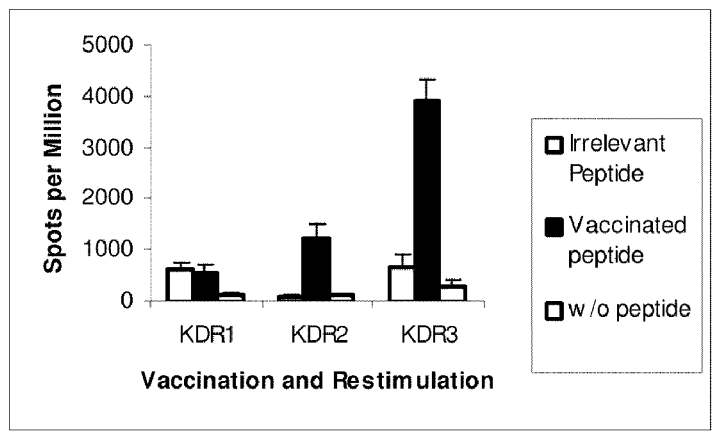

After 1 week in vitro culture in the presence of the vaccinated peptide, the number of IFN-γ secreting cells increased to about 10-20 times more than the background in KDR2 and KDR3 groups, but VEGFR-2/KDR1 group remained negative (FIG. 2B). As shown in FIGS. 2A and 2B, when pulsed with syngeneic VEGFR-2/KDR negative EL4 cell, the background is less than 10% of the positive group. These results indicated that KDR2 and KDR3, but not VEGFR-2/KDR1, break self-tolerance and induce specific immune response in C57BL/6 mice. These findings are in agreement with the RMA-S binding data.

Figure 2C:
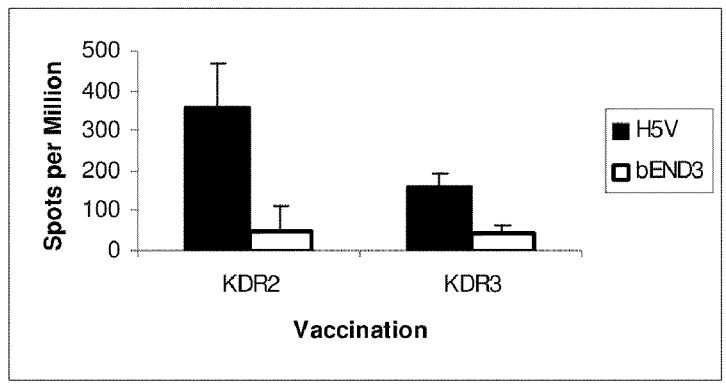

The time course of response differed between peptides, with KDR2 yielding a more rapid response. When stimulated with syngeneic VEGFR-2/KDR expressing cells (H5V), KDR2 vaccinated group had 360 IFN-γ secreting cells per million fresh DLN cells, whereas KDR3 group had 161 per million cells. A lower response was observed following stimulation with allogeneic bEND3 cells (FIG. 2C).

Example 5

MHC Class I Tetramer Binds CTLs Induced by KDR2 and KDR3 Vaccination

The T cell response to vaccination with the VEGFR-2/KDR immunogenic peptides was evaluated using a MHC Class I Tetramer staining assay. Tetrameric MHC Class I complexes including the VEGFR-2/KDR2 immunogenic peptides were used to detect CD8+ T cells that specifically bound to VEGFR-2/KDR. MHC Class I tetramer were from the NIH Tetramer Core Facility at Emory University. 7-AAD and anti-mouse CD8 were from BD Pharmingen. Staining protocol from NIH Tetramer Core Facility was strictly followed. Briefly, $2-3 \times 10^6$ cells were incubated with 7-AAD and appropriate antibodies at 4° C. for 30 minutes, washed 3 times, then fixed with 1% paraformaldehyde. About 100,000 cells were collected by FACSCAN (Becton Dickinson) for each sample. Results were analyzed by CELLQUEST™ software. Dead cells were gated out by staining with 7-AAD.

Figure 3:
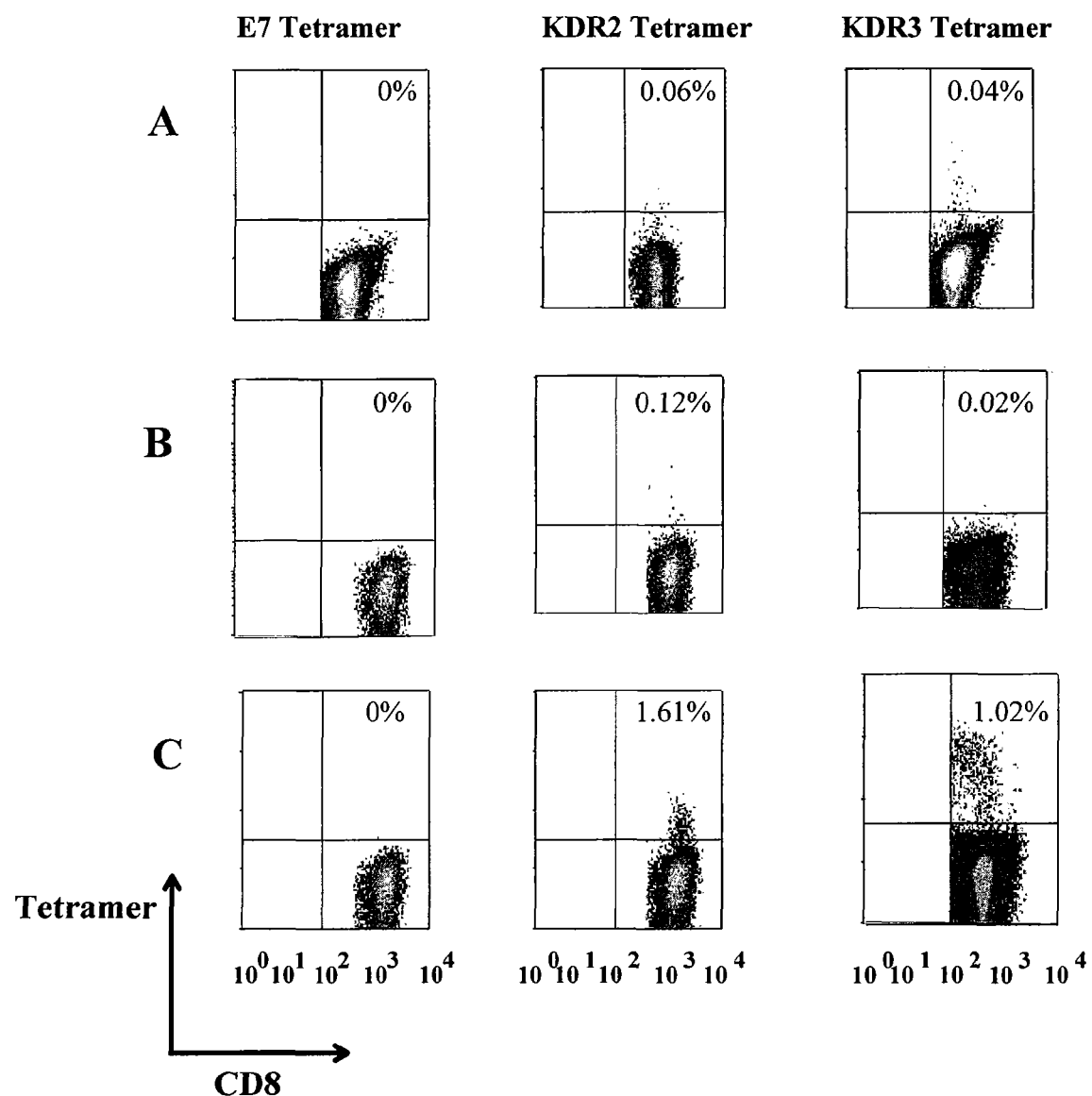
FIG. 3 is a series of flow cytometry scatter plots illustrating tetramer staining of CTLs. Plots are gated on 7-AAD negative and CD8 positive cells: Panel A: Fresh isolated cells; Panel B: spleen cells from naïve mice after restimulated in vitro with peptide KDR2 or KDR3 for 7 days; Panel C: splenocytes from vaccinated mice and restimulated in vitro for 7 days with vaccinated peptides. Left row: H-2 Db-HPV16 E7 49-57 tetramer served as irrelevant control, Middle row: H-2 Db-KDR2 tetramer; Right row: H-2 Db-KDR3 tetramer.
Figure 4A:
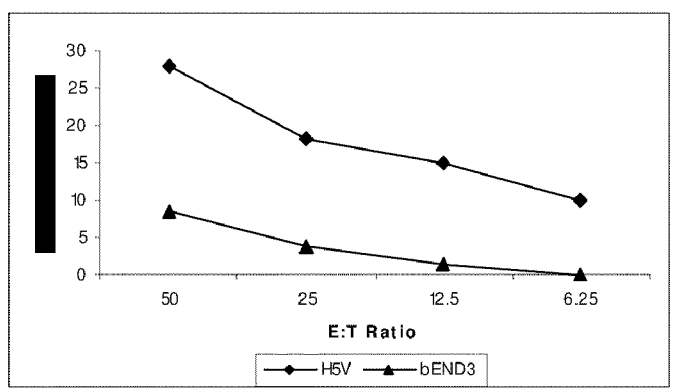
FIGS. 4A-D are line graphs illustrating the results of standard 4 hr $^{51}$Cr release test. Three weeks after immunization, spleen cells were prepared from immunized mice (4-5 mice per group) and restimulated with vaccinated peptides in a 24-well plate in the presence of RPMI 1640 (Invitrogen) with 10% FCS. 10% T-stim was added 48 hours later into the culture media and the cells were incubated for 5 days at 37° C. The CTL activity was tested in a 4-hour $^{51}$Cr release assay. Target cells include VEGFR-2/KDR+H5V (H-2d) and bEND3 (H-2b) endothelial cells, VEGFR-2/KDR-EL4 cells pulsed with peptides or EL4 alone. The percentage of specific lysis was calculated using the formula.
Figure 4B:
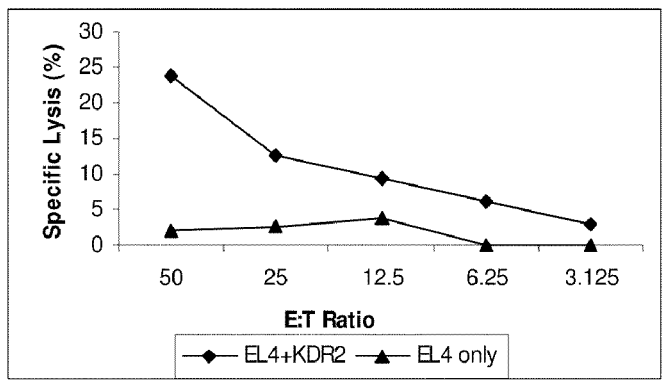
Figure 4C:
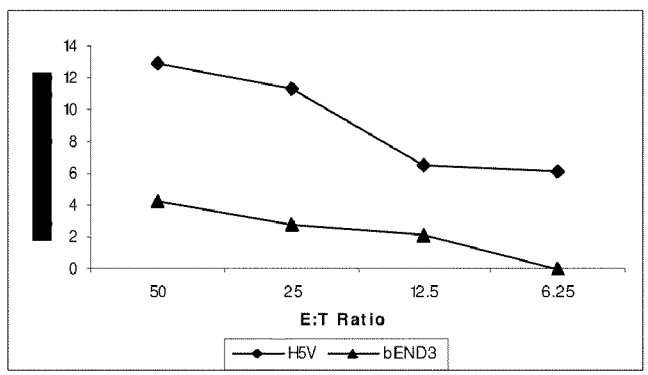
Figure 4D:
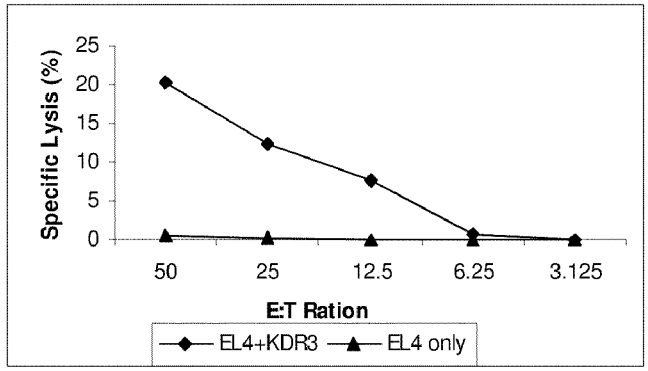

In freshly collected cells, the percentage of CD8+ Tetramer positive cells is low (about 0.05%), in contrast, more than 1% of CD8+ cells were tetramer positive after one week peptide restimulation in vitro (FIG. 3). Thus, about 25 times increase can be seen in mouse spleen cells after 7 days in vitro restimulation. While only 0.02-0.08% of total CD8+ cells from naive mice were tetramer positive even after 7 days in vitro restimulation. As shown in FIG. 3, the non-specific binding of this assay was very low (0.01%).

Example 6

CTLs Induced by Peptides Lyse Tumor Cell Lines Expressing VEGFR-2/KDR

Chromium ($^{51}$Cr) Release Assays were used to determine whether T cells identified as binding to VEGFR-2/KDR specifically targeted endothelial cells. Mice were vaccinated twice with 5 μg GM-CSF, 20 μg anti-CD40 and 100 μg peptide per mice. Briefly, spleen cells were prepared from immunized mice (4-5 mice per group) and restimulated with the vaccinated peptides in 24-well plates in RPMI 1640 (Invitrogen) with 10% FCS. Forty-eight hours later, 10% T-stim (BD Bioscience) was added into the culture media. CTL activity was tested in a 4-hour $^{51}$Cr release assay 5 days later. VEGFR-2/KDR+syngeneic H5V (H-2d), allogeneic bEND3 (H-2b) endothelial cells and VEGFR-2/KDR syngeneic EL4 cells pulsed with peptides or EL4 alone served as target cells. The percentage cytotoxicity was calculated using the formula: (experimental release−spontaneous release)/(maximum release−spontaneous release)×100.

As shown in FIG. 4, at an endothelial cell to T cell ratio (E:T ratio) of 50:1, the percentage of lyses of CTLs induced by KDR2 reach 25% when using EL4 pulsed with KDR2 as targets, and 28% when using H5V, while the control is about 8% and 1% respectively. The percentage of lyses of CTLs induced by KDR3 was found to be lower than that of KDR2, but at E:T ratio at 50:1, the percentage of lyses still reach 13% and 21% when H5V and EL4 pulsed with KDR3 peptide as targets, while the control are 3% and 0.

CTLs induced by KDR2 and KDR3 can lyse H5V cells (H-2b, VEGFR-2/KDR+) and EL4 (H-2b, VEGFR-2/KDR−) pulsed with corresponding VEGFR-2/KDR peptides, but not MHC Class I unmatched bEND3 cell or the MHC matched but VEGFR-2/KDR negative cells (EL4), (FIG. 4). Such a pattern of MHC restricted lyses indicates the role of CTLs and shows KDR2 and KDR3 epitopes are naturally processed by and presented at endothelial cells H5V.

Example 7

Vaccination with KDR2 and KDR3 Peptides Suppresses Angiogenesis In Vivo

To test the effect of VEGFR-2/KDR peptide vaccination on VEGFR-2/KDR induced angiogenesis in vivo, a Matrigel Plug Assay was performed using murine VEGF as pro-angiogenesis factor. C57BL/6 mice (6-8 weeks old) were vaccinated three times at 3-week intervals in the tails. Ten days after the last vaccination, 500 l growth factor reduced Matrigel with or without 100 ng/ml murine VEGF (Pepro Tech) were injected subcutaneously into the right flanks of the mice (four groups). Group one was injected with 0.5 ml growth factor reduced Matrigel alone and served as a negative control. The other 3 groups received 0.5 ml Matrigel containing 100 mg/ml of mVEGF: Group 2 served as a positive control, the remaining two groups received either the adjuvants alone or (G3) or the adjuvants and KDR3 peptides (G4). Plugs were resected after 10 days and were shaken overnight in 2× water before 1 hour of incubation with an equal volume of Drabkin reagent (Sigma) and colorimetric assessment at A540 (Fahmy et al., *Nat. Med.* 9:1026-1032, 2003).

Matrigel without growth factors cannot effectively induce neo-vascularization, while plugs containing 100 ng/ml murine VEGF was enough to induce angiogenesis (FIG. 5 B upper panel). Compared to group that was immunized with adjuvants only, angiogenesis in mice immunized with KDR2 and KDR3 were reduced dramatically (FIGS. 5 A and B lower panel). Hemoglobin contents in the Matrigel plugs were lower in the group (Gr4) vaccinated with VEGFR-2/KDR peptides than that of the group vaccinated with adjuvants only (Gr3), OD540 of the plugs were 0.042±0.047 (n=6) vs. 0.152±0.110 respectively (P<0.05 relative to control group by Student's T test).

Example 8

KDR2 and KDR3 Immunizations Inhibit MC38 Tumor Growth

The murine colon cancer cell line MC38 was used as a model tumor in C57L/B6 mice to evaluate the ability of vaccination with VEGFR-2/KDR peptides to inhibit tumor growth. For the MC38 therapeutic model, $3 \times 10^4$ MC38 cells were injected s.c. into the right flanks of C57BL/6 mice at day 1. Mice were randomized into 3 groups (5 mice each), and were immunized with PBS, adjuvants only or adjuvants plus 100 µg KDR2 and KDR3 peptides twice at 3-week intervals in the tails. Ten days after the last vaccination, mice were injected intravenously with $5 \times 10^4$ MC38 cells. Tumors were measured by caliper twice a week until the mice were sacrificed, when tumor reach 2 millimeter in length. Lungs were removed and fixed in 10% Formaldehyde, then weighed. Student's T test was performed with SPSS software.

There were no significant difference between the adjuvants and PBS groups, but tumor growth in the KDR2 and KDR3 vaccinated group was comparatively slower than the other two groups (FIG. 6). These results indicated vaccination with these two peptides inhibits MC38 tumor growth in mice. Additionally, although VEGFR-2/KDR is also expressed in normal vascular endothelium (albeit at lower levels than in tumor vasculature), no obvious side effects were observed in the animal model described herein, demonstrating that vaccination with VEGFR-2/KDR peptides is likely to be tolerated in vivo.

Example 9

Identification of Human VEGFR-2/KDR Peptides

The sequence of human VEGFR-2/KDR was also evaluated using computer algorithms to identify HLA-A2 binding epitopes. Seven HLA-A2 binding epitopes were identified. The sequences of these peptides are shown in Table 3.

TABLE 2

| Human VEGFR-2/KDR immunogenic peptides | |
|---|---|
| Peptide Sequence | SEQ ID NO: |
| VLLWEIFSL | SEQ ID NO: 5 |
| ALIEGKNKT | SEQ ID NO: 6 |
| AMFFWLLLV | SEQ ID NO: 7 |
| VLLAVALWL | SEQ ID NO: 8 |
| LMTKKNSTFV | SEQ ID NO: 9 |
| FLSTLTIDGV | SEQ ID NO: 10 |
| WLLLVIILRT | SEQ ID NO: 11 |
| VIAMFFWLL | SEQ ID NO: 12 |

Example 10

Exemplary Human VEGFR-2/KDR Peptides Bind HLA-A2

To test the binding affinity of the predicted human peptides for HLA-A2, three exemplary peptides, designated KDR505 (SEQ ID NO:6), KDR775 (SEQ ID NO:7) and KDR1093 (SEQ ID NO:5) were synthesized and evaluated in a T2 binding assay as described by Cerundolo et al., *Nature* 342: 449-452, 1990. In brief, T2 cells were cultured in RPMI1640 with 10% FBS, and grown in 5% $CO_2$ at 37° C. Cells ($1 \times 10^5$) in a volume of 100 µl of RPMI 1640 (serum free) were aliquoted into 96-well, U-bottomed plates and incubated with peptide at a final concentration of 0.1-100 µM plus 5 nM γ2 microglobulin (Cymbus Biotechnology Ltd., Chandlers Ford, Hampshire, United Kingdom) for 18 h at 37° C. in 5% $CO_2$. The level of stabilized HLA-A2 on the surface of the T2 cells was detected using the pan HLA class I monoclonal antibody W6/32 (European Collection of Animal Cell Cultures (ECACC), Porton Down, Salisbury) that recognizes stabilized HLA-A2 complexes. Samples are fixed in 1% paraformaldehyde in PBS prior to analysis and analyzed on a Becton Dickinson FACSCAN®.

As shown in FIG. 7, all three peptides bound HLA-A2 at concentrations of 100 μM. KDR775 bound to MHC molecules at a substantially higher affinity than the other two peptides tested.

Example 11

Human VEGF/KDR Peptides are Immunogenic

To evaluate the ability of the exemplary human peptides to elicit an immune response specific for VEGFR-2, transgenic mice expressing human MHC Class I molecules (HLA-A2) were immunized with the human peptides (KDR505, KDR775 and KDR1093) as described above. Elicited immune responses were evaluated by Elispot assay.

Elispot plates (Millipore, Bedford, Mass.) were coated with 8 μg of anti-gamma interferon (IFN-γ) antibody per ml in sterile phosphate-buffered saline (PBS) overnight at 4° C. Plates were washed and then blocked with RPMI 1640 with 10% FBS. Fresh splenocytes or cells after 1 week in vitro restimulation were used as effectors. $5 \times 10^5$ effector cells were co-cultured overnight with or without $2 \times 10^5$ irradiated (3,000 rads) C1R.A2 cells (human) in 200 μl media at 37° C., 5% CO2 in the presence of appropriate concentration of peptide.

A representative assay in the presence and absence of C1R.A2 cells is illustrated in FIGS. 8A and B, respectively. These results demonstrate that the exemplary human VEGFR-2/KDR peptides elicit an immune response against VEGFR-2/KDR.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

We claim:

1. An isolated or synthetic peptide, comprising FLSTLTIDGV (SEQ ID NO: 10) and wherein the isolated or synthetic peptide is no more than 30 amino acids in length and binds to a Major Histocompatibility (MHC) Class I molecule.

2. The peptide of claim 1, wherein the peptide binds to an HLA-A2 molecule and is no more than 12 amino acids in length.

3. A pharmaceutical composition comprising: the isolated or synthetic peptide of claim 1 and a pharmaceutically acceptable carrier.

4. The pharmaceutical composition of claim 3, comprising a plurality of different isolated or synthetic Vascular Endothelial Growth Factor Receptor 2 (VEGFR-2) peptides that bind to a Major Histocompatibility (MHC) Class I molecule.

5. The pharmaceutical composition of claim 3, wherein the pharmaceutical composition comprises a cytokine.

6. The pharmaceutical composition of claim 3, further comprising an adjuvant.

7. The isolated or synthetic peptide of claim 1, wherein the peptide consists of the amino acid sequence set forth as SEQ ID NO: 10.

8. The isolated or synthetic peptide of claim 1, wherein the peptide is 10 to 12 amino acids in length.

9. The isolated or synthetic peptide of claim 1, wherein the peptide is 13 amino acids in length.

10. The isolated or synthetic peptide of claim 1, wherein the peptide is 15 amino acids in length.

* * * * *

UNITED STATES PATENT AND TRADEMARK OFFICE
CERTIFICATE OF CORRECTION

PATENT NO.         : 8,378,071 B2
APPLICATION NO.    : 12/402401
DATED              : February 19, 2013
INVENTOR(S)        : Khleif and Dong It is certified that error appears in the above-identified patent and that said Letters Patent is hereby corrected as shown below:

In the Specification:

Column 2, line 46, "of a several" should read -- of several --.

Column 4, line 3, "tumor reach 2" should read -- tumors reached 2 --.

Column 9, line 55, "such an HLA" should read -- such as a HLA --.

Column 13, line 63, "substitutions" should read -- substitution --.

Column 17, line 3, "therapeutic" should read -- therapeutic response --.

Column 25, line 63, "CO2" should read -- $CO_2$ --.

Column 27, line 6, "H-2 Db" should read -- H-2Db --.

Column 27, line 9, "H-2 Db" should read -- H-2Db --.

Column 27, line 10, "H-2 Db" should read -- H-2Db --.

Column 27, line 13, "H-2 Db" should read -- H-2Db --.

Column 27, line 45, "CO2" should read -- $CO_2$ --.

Signed and Sealed this
Thirteenth Day of August, 2013

Teresa Stanek Rea
*Acting Director of the United States Patent and Trademark Office*